(12) United States Patent
Dale et al.

(10) Patent No.: US 11,364,117 B2
(45) Date of Patent: Jun. 21, 2022

(54) BRAID CONNECTIONS FOR PROSTHETIC HEART VALVES

(71) Applicant: St. Jude Medical, Cardiology Division, Inc., St. Paul, MN (US)

(72) Inventors: Theodore Paul Dale, Corcoran, MN (US); Katherine A. Ahmann, Arden Hills, MN (US); Brian Joseph Perszyk, Shoreview, MN (US); Mathias Charles Glimsdale, St. Michael, MN (US); Kristopher Henry Vietmeier, Monticello, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 253 days.

(21) Appl. No.: 16/578,512

(22) Filed: Sep. 23, 2019

(65) Prior Publication Data

US 2020/0113683 A1    Apr. 16, 2020

Related U.S. Application Data

(60) Provisional application No. 62/745,528, filed on Oct. 15, 2018.

(51) Int. Cl.
*A61F 2/24* (2006.01)

(52) U.S. Cl.
CPC .... *A61F 2/2418* (2013.01); *A61F 2210/0014* (2013.01); *A61F 2220/0025* (2013.01); *A61F 2220/0033* (2013.01); *A61F 2220/0075* (2013.01); *A61F 2250/0039* (2013.01); *A61F 2250/0069* (2013.01)

(58) Field of Classification Search
CPC ... A61F 2/2475–2002/2424; A61F 2250/0069; A61F 2002/077
See application file for complete search history.

(56) References Cited

U.S. PATENT DOCUMENTS

| 3,657,744 A | 4/1972 | Ersek |
| 4,275,469 A | 6/1981 | Gabbay |

(Continued)

FOREIGN PATENT DOCUMENTS

| DE | 19857887 A1 | 7/2000 |
| DE | 10121210 B4 | 11/2005 |

(Continued)

OTHER PUBLICATIONS

"Catheter-Implanted Prosthetic Heart Valves: Transluminal Catheter Implantation of a New Expandable Artificial Heart Valve in the Descending Thoracic Aorta in Isolated Vessels and Closed Chest Pigs", Knudsen et al., The International Journal of Artificial Organs, vol. 16, No. 5, May 1993, pp. 253-262.

(Continued)

*Primary Examiner* — Rebecca S Preston
(74) *Attorney, Agent, or Firm* — Wei & Sleman LLP

(57) ABSTRACT

A prosthetic heart valve may include a stent, a valve assembly, a flange, and a plurality of coupling tubes. The stent may have a collapsed condition, an expanded condition, and a plurality of cells arranged in circumferential rows, the stent having a longitudinal axis, an inflow end and an outflow end. The valve assembly may be disposed within the stent. The flange may comprise a plurality of braided wires and may have a flared portion. The plurality of coupling tubes may couple the flange to the stent so that the flared portion is adjacent the inflow end of the stent. Each of the coupling tubes may have a first end receiving corresponding ones of the braided wires and a second end coupled to a corresponding portion of the stent.

20 Claims, 19 Drawing Sheets

(56) References Cited

U.S. PATENT DOCUMENTS

| | | | |
|---|---|---|---|
| 4,491,986 | A | 1/1985 | Gabbay |
| 4,759,758 | A | 7/1988 | Gabbay |
| 4,878,906 | A | 11/1989 | Lindemann et al. |
| 4,922,905 | A | 5/1990 | Strecker |
| 4,994,077 | A | 2/1991 | Dobben |
| 5,411,552 | A | 5/1995 | Andersen et al. |
| 5,415,664 | A | 5/1995 | Pinchuk |
| 5,480,423 | A | 1/1996 | Ravenscroft et al. |
| 5,843,167 | A | 12/1998 | Dwyer et al. |
| 5,855,601 | A | 1/1999 | Bessler et al. |
| 5,935,163 | A | 8/1999 | Gabbay |
| 5,961,549 | A | 10/1999 | Nguyen et al. |
| 6,045,576 | A | 4/2000 | Starr et al. |
| 6,077,297 | A | 6/2000 | Robinson et al. |
| 6,083,257 | A | 7/2000 | Taylor et al. |
| 6,090,140 | A | 7/2000 | Gabbay |
| 6,214,036 | B1 | 4/2001 | Letendre et al. |
| 6,264,691 | B1 | 7/2001 | Gabbay |
| 6,267,783 | B1 | 7/2001 | Letendre et al. |
| 6,368,348 | B1 | 4/2002 | Gabbay |
| 6,419,695 | B1 | 7/2002 | Gabbay |
| 6,458,153 | B1 | 10/2002 | Bailey et al. |
| 6,468,660 | B2 | 10/2002 | Ogle et al. |
| 6,488,702 | B1 | 12/2002 | Besselink |
| 6,517,576 | B2 | 2/2003 | Gabbay |
| 6,533,810 | B2 | 3/2003 | Hankh et al. |
| 6,582,464 | B2 | 6/2003 | Gabbay |
| 6,610,088 | B1 | 8/2003 | Gabbay |
| 6,623,518 | B2 | 9/2003 | Thompson et al. |
| 6,652,578 | B2 | 11/2003 | Bailey et al. |
| 6,685,625 | B2 | 2/2004 | Gabbay |
| 6,716,244 | B2 | 4/2004 | Klaco |
| 6,719,789 | B2 | 4/2004 | Cox |
| 6,730,118 | B2 | 5/2004 | Spenser et al. |
| 6,783,556 | B1 | 8/2004 | Gabbay |
| 6,790,230 | B2 | 9/2004 | Beyersdorf et al. |
| 6,814,746 | B2 | 11/2004 | Thompson et al. |
| 6,830,584 | B1 | 12/2004 | Seguin |
| 6,869,444 | B2 | 3/2005 | Gabbay |
| 6,893,460 | B2 | 5/2005 | Spenser et al. |
| 6,908,481 | B2 | 6/2005 | Cribier |
| 6,951,573 | B1 | 10/2005 | Dilling |
| 7,018,406 | B2 | 3/2006 | Seguin et al. |
| 7,025,780 | B2 | 4/2006 | Gabbay |
| 7,137,184 | B2 | 11/2006 | Schreck |
| 7,160,322 | B2 | 1/2007 | Gabbay |
| 7,195,641 | B2 | 3/2007 | Palmaz et al. |
| 7,247,167 | B2 | 7/2007 | Gabbay |
| 7,267,686 | B2 | 9/2007 | DiMatteo et al. |
| 7,276,078 | B2 | 10/2007 | Spenser et al. |
| 7,311,730 | B2 | 12/2007 | Gabbay |
| 7,320,704 | B2 | 1/2008 | Lashinski et al. |
| 7,329,278 | B2 | 2/2008 | Seguin et al. |
| 7,374,573 | B2 | 5/2008 | Gabbay |
| 7,381,218 | B2 | 6/2008 | Schreck |
| 7,381,219 | B2 | 6/2008 | Salahieh et al. |
| 7,452,371 | B2 | 11/2008 | Pavcnik et al. |
| 7,510,572 | B2 | 3/2009 | Gabbay |
| 7,510,575 | B2 | 3/2009 | Spenser et al. |
| 7,524,331 | B2 | 4/2009 | Birdsall |
| 7,534,261 | B2 | 5/2009 | Friedman |
| RE40,816 | E | 6/2009 | Taylor et al. |
| 7,585,321 | B2 | 9/2009 | Cribier |
| 7,628,805 | B2 | 12/2009 | Spenser et al. |
| 7,682,390 | B2 | 3/2010 | Seguin |
| 7,708,775 | B2 | 5/2010 | Rowe et al. |
| 7,731,742 | B2 | 6/2010 | Schlick et al. |
| 7,748,389 | B2 | 7/2010 | Salahieh et al. |
| 7,780,725 | B2 | 8/2010 | Haug et al. |
| 7,799,069 | B2 | 9/2010 | Bailey et al. |
| 7,803,185 | B2 | 9/2010 | Gabbay |
| 7,824,442 | B2 | 11/2010 | Salahieh et al. |
| 7,837,727 | B2 | 11/2010 | Goetz et al. |
| 7,846,203 | B2 | 12/2010 | Cribier |
| 7,846,204 | B2 | 12/2010 | Letac et al. |
| 7,857,845 | B2 | 12/2010 | Stacchino et al. |
| 7,892,281 | B2 | 2/2011 | Seguin et al. |
| 7,914,569 | B2 | 3/2011 | Nguyen et al. |
| 7,959,666 | B2 | 6/2011 | Salahieh et al. |
| 7,959,672 | B2 | 6/2011 | Salahieh et al. |
| 7,972,378 | B2 | 7/2011 | Tabor et al. |
| 7,988,724 | B2 | 8/2011 | Salahieh et al. |
| 7,993,394 | B2 | 8/2011 | Hariton et al. |
| 8,016,877 | B2 | 9/2011 | Seguin et al. |
| D648,854 | S | 11/2011 | Braido |
| 8,048,153 | B2 | 11/2011 | Salahieh et al. |
| 8,052,741 | B2 | 11/2011 | Bruszewski et al. |
| 8,052,749 | B2 | 11/2011 | Salahieh et al. |
| 8,052,750 | B2 | 11/2011 | Tuval et al. |
| 8,062,355 | B2 | 11/2011 | Figulla et al. |
| 8,075,611 | B2 | 12/2011 | Millwee et al. |
| D652,926 | S | 1/2012 | Braido |
| D652,927 | S | 1/2012 | Braido et al. |
| D653,341 | S | 1/2012 | Braido et al. |
| D653,342 | S | 1/2012 | Braido et al. |
| D653,343 | S | 1/2012 | Ness et al. |
| D654,169 | S | 2/2012 | Braido |
| D654,170 | S | 2/2012 | Braido et al. |
| 8,137,398 | B2 | 3/2012 | Tuval et al. |
| 8,142,497 | B2 | 3/2012 | Friedman |
| D660,432 | S | 5/2012 | Braido |
| D660,433 | S | 5/2012 | Braido et al. |
| D660,967 | S | 5/2012 | Braido et al. |
| 8,182,528 | B2 | 5/2012 | Salahieh et al. |
| 8,221,493 | B2 | 7/2012 | Boyle et al. |
| 8,230,717 | B2 | 7/2012 | Matonick |
| 8,231,670 | B2 | 7/2012 | Salahieh et al. |
| 8,252,051 | B2 | 8/2012 | Chau et al. |
| 8,308,798 | B2 | 11/2012 | Pintor et al. |
| 8,313,525 | B2 | 11/2012 | Fuval et al. |
| 8,323,335 | B2 | 12/2012 | Rowe et al. |
| 8,323,336 | B2 | 12/2012 | Hill et al. |
| 8,343,213 | B2 | 1/2013 | Salahieh et al. |
| 8,348,995 | B2 | 1/2013 | Fuval et al. |
| 8,348,996 | B2 | 1/2013 | Fuval et al. |
| 8,348,998 | B2 | 1/2013 | Pintor et al. |
| 8,366,769 | B2 | 2/2013 | Huynh et al. |
| 8,403,983 | B2 | 3/2013 | Quadri et al. |
| 8,408,214 | B2 | 4/2013 | Spenser |
| 8,414,643 | B2 | 4/2013 | Tuval et al. |
| 8,425,593 | B2 | 4/2013 | Braido et al. |
| 8,449,599 | B2 | 5/2013 | Chau et al. |
| 8,449,604 | B2 | 5/2013 | Moaddeb et al. |
| D684,692 | S | 6/2013 | Braido |
| 8,454,686 | B2 | 6/2013 | Alkhatib |
| 8,500,798 | B2 | 8/2013 | Rowe et al. |
| 8,568,474 | B2 | 10/2013 | Yeung et al. |
| 8,579,962 | B2 | 11/2013 | Salahieh et al. |
| 8,579,966 | B2 | 11/2013 | Seguin et al. |
| 8,585,755 | B2 | 11/2013 | Chau et al. |
| 8,591,575 | B2 | 11/2013 | Cribier |
| 8,597,349 | B2 | 12/2013 | Alkhatib |
| 8,603,159 | B2 | 12/2013 | Seguin et al. |
| 8,603,160 | B2 | 12/2013 | Salahieh et al. |
| 8,613,765 | B2 | 12/2013 | Bonhoeffer et al. |
| 8,623,074 | B2 | 1/2014 | Ryan |
| 8,652,204 | B2 | 2/2014 | Quill et al. |
| 8,663,322 | B2 | 3/2014 | Keranen |
| 8,668,733 | B2 | 3/2014 | Haug et al. |
| 8,685,080 | B2 | 4/2014 | White |
| 8,728,154 | B2 | 5/2014 | Alkhatib |
| 8,747,459 | B2 | 6/2014 | Nguyen et al. |
| 8,764,820 | B2 | 7/2014 | Dehdashtian et al. |
| 8,795,357 | B2 | 8/2014 | Yohanan et al. |
| 8,801,776 | B2 | 8/2014 | House et al. |
| 8,808,356 | B2 | 8/2014 | Braido et al. |
| 8,828,078 | B2 | 9/2014 | Salahieh et al. |
| 8,834,563 | B2 | 9/2014 | Righini |
| 8,840,661 | B2 | 9/2014 | Manasse |
| 8,840,663 | B2 | 9/2014 | Salahieh et al. |
| 8,876,894 | B2 | 11/2014 | Tuval et al. |
| 8,876,895 | B2 | 11/2014 | Tuval et al. |
| 8,940,040 | B2 | 1/2015 | Shahriari |
| 8,945,209 | B2 | 2/2015 | Bonyuet et al. |

| | | |
|---|---|---|
| 8,961,595 B2 | 2/2015 | Alkhatib |
| 8,974,523 B2 | 3/2015 | Thill et al. |
| 8,974,524 B2 | 3/2015 | Yeung et al. |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0111111 A1 | 6/2004 | Lin |
| 2004/0210304 A1 | 10/2004 | Seguin et al. |
| 2004/0260389 A1 | 12/2004 | Case et al. |
| 2005/0096726 A1 | 5/2005 | Sequin et al. |
| 2005/0137682 A1 | 6/2005 | Justino |
| 2005/0137695 A1 | 6/2005 | Salahieh et al. |
| 2005/0137697 A1 | 6/2005 | Salahieh et al. |
| 2005/0203605 A1 | 9/2005 | Dolan |
| 2005/0240200 A1 | 10/2005 | Bergheim |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0161249 A1 | 7/2006 | Realyvasquez et al. |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0276027 A1 | 11/2009 | Glynn |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0208283 A1 | 8/2011 | Rust |
| 2011/0264206 A1 | 10/2011 | Tabor |
| 2012/0035722 A1 | 2/2012 | Tuval |
| 2012/0078347 A1 | 3/2012 | Braido et al. |
| 2012/0101572 A1 | 4/2012 | Kovalsky et al. |
| 2012/0123529 A1 | 5/2012 | Levi et al. |
| 2012/0303116 A1 | 11/2012 | Gorman, III et al. |
| 2013/0274873 A1 | 10/2013 | Delaloye et al. |
| 2014/0121763 A1 | 5/2014 | Duffy et al. |
| 2014/0155997 A1 | 6/2014 | Braido |
| 2014/0214159 A1 | 7/2014 | Vidlund et al. |
| 2014/0228946 A1 | 8/2014 | Chau et al. |
| 2014/0303719 A1 | 10/2014 | Cox et al. |
| 2014/0324164 A1 | 10/2014 | Gross et al. |
| 2014/0343671 A1 | 11/2014 | Yohanan et al. |
| 2014/0350668 A1 | 11/2014 | Delaloye et al. |
| 2014/0350669 A1 | 11/2014 | Gillespie et al. |
| 2017/0049564 A1* | 2/2017 | Board .................. A61F 2/2418 |
| 2018/0116798 A1* | 5/2018 | Perszyk .................. A61F 2/2418 |
| 2019/0183639 A1* | 6/2019 | Moore .................. A61F 2/2418 |

FOREIGN PATENT DOCUMENTS

| | | |
|---|---|---|
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1584306 A1 | 10/2005 |
| EP | 1598031 A2 | 11/2005 |
| EP | 1360942 B1 | 12/2005 |
| EP | 1926455 A2 | 6/2008 |
| EP | 2537487 A1 | 12/2012 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 01028459 A1 | 4/2001 |
| WO | 2001049213 A2 | 7/2001 |
| WO | 0154625 A1 | 8/2001 |
| WO | 01056500 A2 | 8/2001 |
| WO | 0176510 A2 | 10/2001 |
| WO | 2002036048 A1 | 5/2002 |
| WO | 0247575 A2 | 6/2002 |
| WO | 02067782 A2 | 9/2002 |
| WO | 03047468 A1 | 6/2003 |
| WO | 2005070343 A1 | 8/2005 |
| WO | 06073626 A2 | 7/2006 |
| WO | 07071436 A2 | 6/2007 |
| WO | 08070797 A2 | 6/2008 |
| WO | 10008548 A2 | 1/2010 |
| WO | 2010008549 A1 | 1/2010 |
| WO | 2010096176 A1 | 8/2010 |
| WO | 2010098857 A1 | 9/2010 |

OTHER PUBLICATIONS

"Closed Heart Surgery: Back to the Future", Samuel V. Lichtenstein, The Journal of Thoracic and Cardiovascular Surgery, vol. 131, No. 5, May 2006, pp. 941-943.

"Direct-Access Valve Replacement", Christoph H. Huber, et al., Journal of the American College of Cardiology, vol. 46, No. 2, (Jul. 19, 2005).

"Minimally invasive cardiac surgery", M. J. Mack, Surgical Endoscopy, 2006, 20:S488-S492, DOI: 10.1007/s00464-006-0110-8 (presented Mar. 23, 2006).

"Percutaneous Aortic Valve Implantation Retrograde From the Femoral Artery", John G. Webb et al., Circulation, 2006; 113:842-850 (Feb. 6, 2006).

"Percutaneous Aortic Valve Replacement: Resection Before Implantation", Quaden, Rene et al., European J. of Cardio-Thoracic Surgery, vol. 27, No. 5, May 2005, pp. 836-840.

"Transapical aortic valve implantation: an animal feasibility study"; Todd M. Dewey et al., The annals of thoracic surgery 2006; 82: 110-6 (Feb. 13, 2006).

"Transapical Approach for Sutureless Stent-Fixed Aortic Valve Implantation: Experimental Results", Th. Walther et al., European Journal of Cardio-Thoracic Surgery, vol. 29, No. 5, May 2006, pp. 703-708.

"Transapical Transcatheter Aortic Valve Implantation in Humans", Samuel V. Lichtenstein et al., Circulation. 2006; 114: 591-596 (Jul. 31, 2006).

"Transcatheter Umbrella Closure of Valvular and Paravalvular Leaks", Hourihan et al., Journal of the American College of Cardiology, vol. 20, No. 6, Nov. 1992, pp. 1371-1377.

"Transluminal Aortic Valve Placement. A Feasability Study with a Newly Designed Collapsible Aortic Valve", Moazami et al., ASAIO Journal, vol. 42, No. 5, 1996, pp. M381-M385.

"Transluminal Catheter Implanted Prosthetic Heart Valves", Andersen, H. R., International Journal of Angiology, vol. 7, No. 2, Mar. 1998, pp. 102-106.

"Transluminal Implantation of Artificial Heart Valves", Andersen, H. R., et al., European Heart Journal, vol. 13, No. 5, May 1992, pp. 704-708.

Buellesfeld et al., "Treatment of Paravalvular Leaks Through Inverventional Techniques", Multimedia Manual of Cardithoracic Surgery, Department of Cardiology, Ben University Hospital, Jan. 2011.

De Cicco, et al., "Aortic Valve Periprosthetic Leakage: Anatomic Observations and Surgical Results", The Annals of Thoracic Surgery, vol. 79, No. 5, May 2005, pp. 1480-1485.

Gössl and Rihal, "Percutaneous Treatment of Aortic and Mitral Valve Paravalvular Regurgitation", Current Cardiology Reports, vol. 15, No. 8, Aug. 2013, pp. 1-8.

Heat Advisor, "Heart repairs without surgery. Minimally invasive procedures aim to correct valve leakage", Sep. 2004, PubMed ID 15586429.

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

Muñoz, Daniel Rodríguez, Carla Lázaro Rivera, and José Luis Zamorano Gómez, "Guidance of Treatment of Perivalvular Prosthetic Leaks", Current Cardiology Reports, vol. 16, No. 1, Nov. 2013, pp. 1-6.

Rohde, I., Masch, J.-M., Theisen-Kunde, D., Marczynski-Buhlow, M., Bombien Quaden, R., Lutter, G. and Brinkmann, R., "Resection of Calcified Aortic Heart Leaflets In Vitro by Q-Switched 2?μm Microsecond Laser Radiation", Journal of Cardiac Surgery, vol. 30, No. 2, Feb. 2015, pp. 157-162. doi: 10.1111/jocs.12481.

Ruiz, Carlos, Overview of PRE-CE Mark Transcatheter Aortic Valve Technologies, Euro PCR, dated May 25, 2010.

Swiatkiewicz et al., "Percutaneous Closure of Mitral Perivalvular Leak", Kardiologia Polska, vol. 67, No. 7, 2009, pp. 762-764.

Transcatheter Valve Repair, Hijazi et al., CRC Press, Jan. 2006, pp. 165-186.

U.S. Appl. No. 29/375,243, filed Sep. 20, 2010—Braido, et al., U.S. Appl. No. 29/375,243, filed Sep. 20, 2010, titled "Surgical Stent Assembly".

* cited by examiner

BRAID CONNECTIONS FOR PROSTHETIC HEART VALVES

CROSS-REFERENCE TO RELATED APPLICATIONS

The present application claims the benefit of the filing date of U.S. Provisional Patent Application No. 62/745,528 filed Oct. 15, 2018, the disclosure of which is hereby incorporated by reference herein.

BACKGROUND

The present disclosure relates to heart valve replacement and, in particular, to collapsible prosthetic heart valves. More particularly, the present disclosure relates to collapsible prosthetic heart valves for use in the mitral valve annulus.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve is generally first collapsed or crimped to reduce its circumferential size.

When a collapsed prosthetic valve has been delivered to the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

BRIEF SUMMARY

A prosthetic heart valve may include a stent, a valve assembly, a flange, and a plurality of coupling tubes. The stent may have a collapsed condition, an expanded condition, and a plurality of cells arranged in circumferential rows, the stent having a longitudinal axis, an inflow end and an outflow end. The valve assembly may be disposed within the stent. The flange may comprise a plurality of braided wires and may have a flared portion. The plurality of coupling tubes may couple the flange to the stent so that the flared portion is adjacent the inflow end of the stent. Each of the coupling tubes may have a first end receiving corresponding ones of the braided wires and a second end coupled to a corresponding portion of the stent.

DETAILED DESCRIPTION

Blood flows through the mitral valve from the left atrium to the left ventricle. As used herein, the term "inflow end," when used in connection with a prosthetic mitral heart valve, refers to the end of the heart valve closest to the left atrium when the heart valve is implanted in a patient, whereas the term "outflow end," when used in connection with a prosthetic mitral heart valve, refers to the end of the heart valve closest to the left ventricle when the heart valve is implanted in a patient. Also, as used herein, the terms "substantially," "generally," and "about" are intended to mean that slight deviations from absolute are included within the scope of the term so modified. Generally, materials described as being suitable for components in one embodiment of the disclosure may also be suitable for similar or identical components described in other embodiments.

Figure 1:
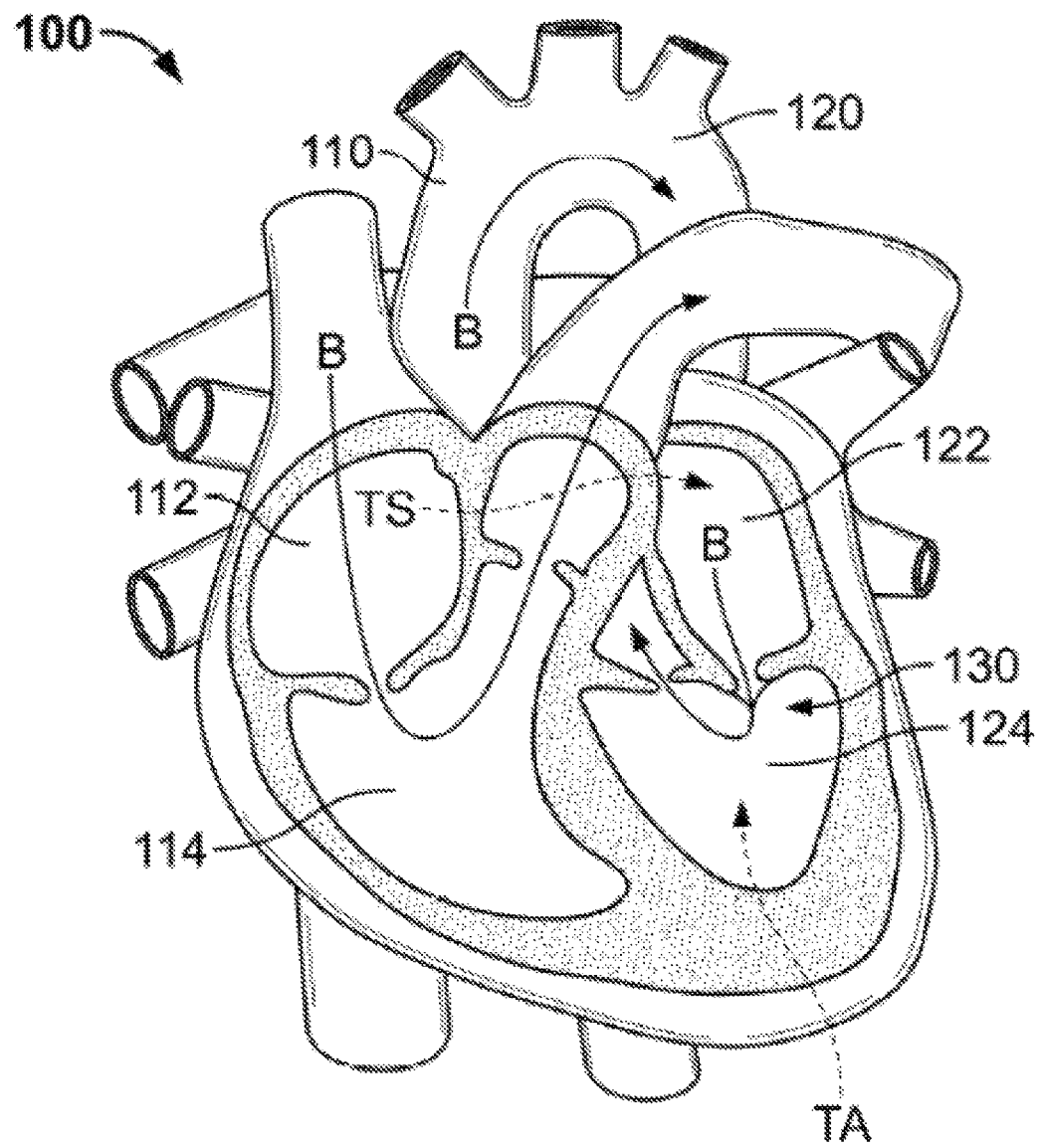
FIG. 1 is a highly schematic cutaway representation of a human heart showing various delivery approaches.

FIG. 1 is a highly schematic cutaway representation of human heart 100. The human heart includes two atria and two ventricles: right atrium 112 and left atrium 122, and right ventricle 114 and left ventricle 124. Heart 100 further includes aorta 110 and aortic arch 120. Disposed between left atrium 122 and left ventricle 124 is mitral valve 130. Mitral valve 130, also known as the bicuspid valve or left atrioventricular valve, is a dual-flap valve that opens as a result of increased pressure in left atrium 122 as it fills with blood. As atrial pressure increases above that of left ventricle 124, mitral valve 130 opens and blood passes into left ventricle 124. Blood flows through heart 100 in the direction shown by arrows "B".

A dashed arrow, labeled "TA", indicates a transapical approach for implanting a prosthetic heart valve, in this case to replace the mitral valve. In transapical delivery, a small incision is made between the ribs and into the apex of left ventricle 124 to deliver the prosthetic heart valve to the target site. A second dashed arrow, labeled "TS", indicates a transseptal approach for implanting a prosthetic heart valve in which the valve is passed through the septum between right atrium 112 and left atrium 122. Other approaches for implanting a prosthetic heart valve are also possible.

Figure 2:
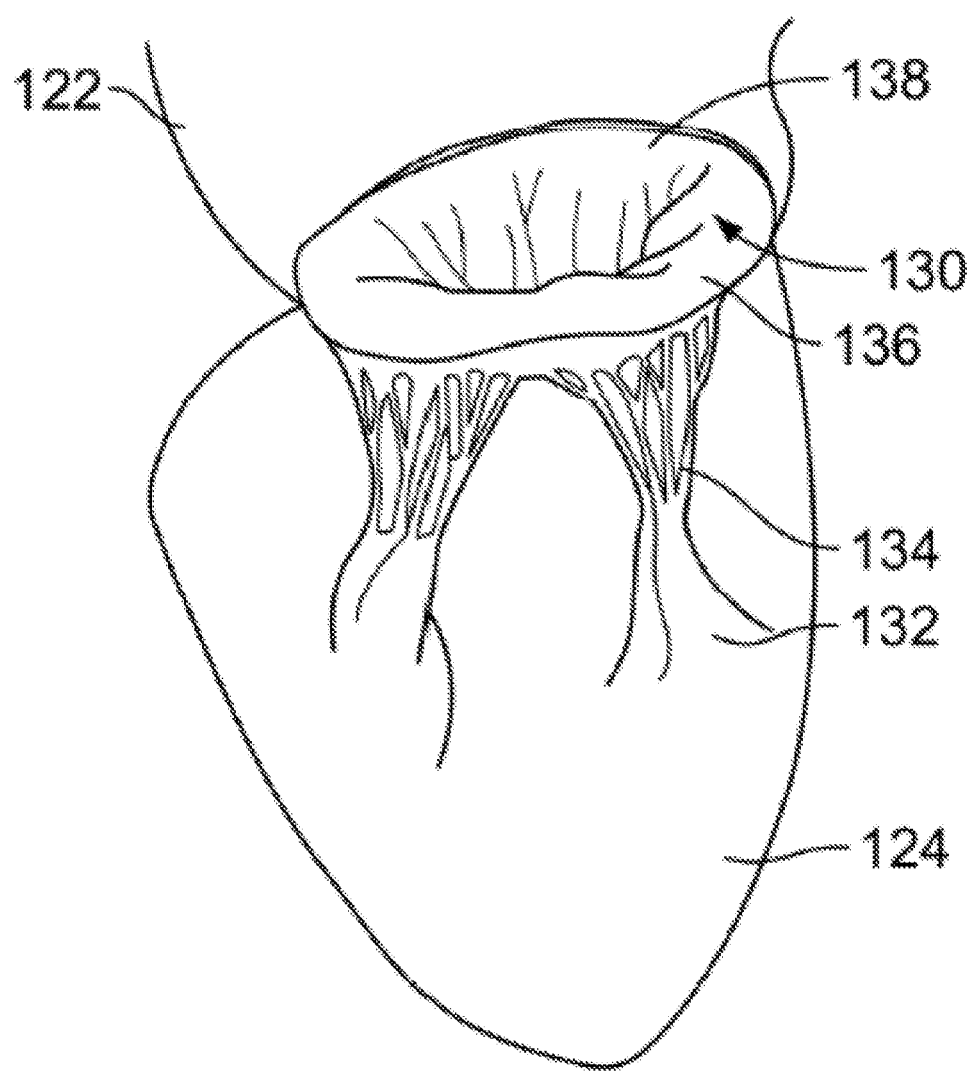
FIG. 2 is a highly schematic representation of a native mitral valve and associated cardiac structures.

FIG. 2 is a more detailed schematic representation of native mitral valve 130 and its associated structures. As previously noted, mitral valve 130 includes two flaps or leaflets, posterior leaflet 136 and anterior leaflet 138, disposed between left atrium 122 and left ventricle 124. Cordlike tendons, known as chordae tendineae 134, connect the two leaflets 136, 138 to the medial and lateral papillary muscles 132. During atrial systole, blood flows from higher pressure in left atrium 122 to lower pressure in left ventricle 124. When left ventricle 124 contracts in ventricular systole, the increased blood pressure in the chamber pushes leaflets 136, 138 to close, preventing the backflow of blood into left atrium 122. Since the blood pressure in left atrium 122 is much lower than that in left ventricle 124, leaflets 136, 138 attempt to evert to the low pressure regions. Chordae tendineae 134 prevent the eversion by becoming tense, thus pulling on leaflets 136, 138 and holding them in the closed position.

Figure 3A:
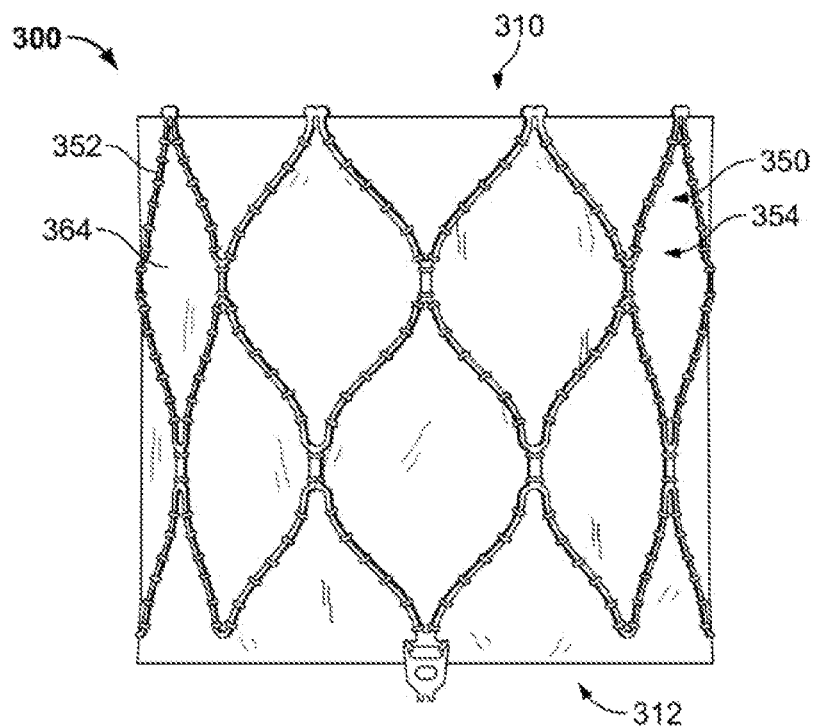
FIG. 3A is a side view of a prosthetic heart valve according to the prior art.
Figure 3B:
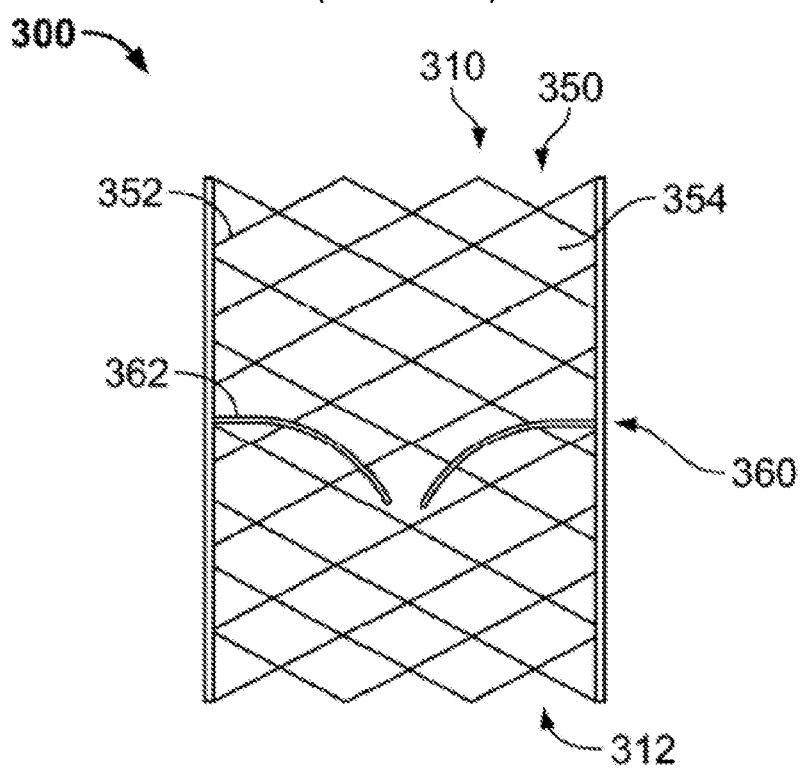
FIG. 3B is a highly schematic longitudinal cross-section of the prosthetic heart valve of FIG. 3A.

FIGS. 3A and 3B are a side view and a longitudinal cross-sectional view of prosthetic heart valve 300, respectively, according to the prior art. Prosthetic heart valve 300 is a collapsible prosthetic heart valve designed to replace the function of the native mitral valve of a patient, such as native mitral valve 130 of FIGS. 1-2. Generally, prosthetic valve 300 has a substantially cylindrical shape with inflow end 310 and outflow end 312. When used to replace native mitral valve 130, prosthetic valve 300 may have a low profile so as to not cause obstruction of the left ventricle outflow tract.

Prosthetic heart valve 300 may include stent 350, which may be formed from biocompatible materials that are capable of self-expansion, such as, for example, shape-memory alloys including nitinol. Stent 350 may include a plurality of struts 352 that form cells 354 connected to one another in one or more annular rows around the stent. Cells 354 may all be of substantially the same size around the perimeter and along the length of stent 350. Alternatively, cells 354 near inflow end 310 may be larger than the cells near outflow end 312. Stent 350 may be expandable to provide a radial force to assist with positioning and stabilizing prosthetic heart valve 300 in the native valve annulus.

Prosthetic heart valve 300 may also include a substantially cylindrical valve assembly 360 including a plurality of leaflets 362 (FIG. 3B) attached to a cuff 364 (FIG. 3A). Leaflets 362 replace the function of native mitral valve leaflets 136 and 138 described above with reference to FIG. 2. That is, leaflets 362 coapt with one another to function as a one-way valve. The valve assembly 360 of prosthetic heart valve 300 may include two or three leaflets, but it should be appreciated that prosthetic heart valve 300 may have more than three leaflets. Both cuff 364 and leaflets 362 may be wholly or partly formed of any suitable biological material, such as bovine or porcine pericardium, or polymers, such as polytetrafluoroethylene (PTFE), urethanes and the like. Valve assembly 360 may be secured to stent 350 by suturing to struts 352 or by using tissue glue, ultrasonic welding, or other suitable methods.

Figure 4A:
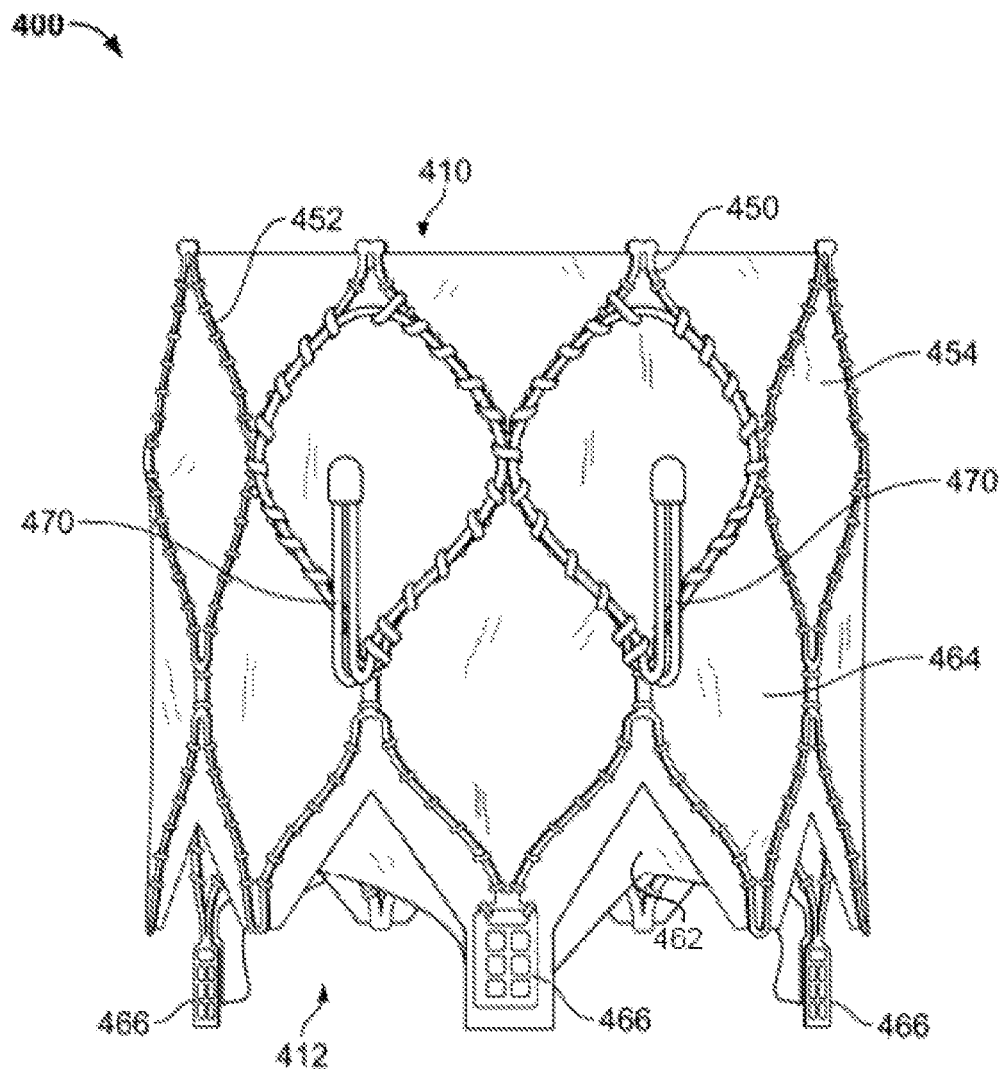
FIG. 4A is a side view of a prosthetic heart valve according to an aspect of the disclosure.

FIG. 4A is a side view of a prosthetic heart valve 400 in accordance with one embodiment of the disclosure. Prosthetic heart valve 400 may be similar or identical to prosthetic heart valve 300 in certain respects. For example, prosthetic heart valve 400 is collapsible and expandable and designed to replace a native mitral valve, having a substantially cylindrical shape with an inflow end 410 and an outflow end 412. It should be understood that prosthetic heart valve 400 is not limited to replacement of mitral valves, and may be used to replace other heart valves. Prosthetic heart valve 400 may include stent 450, which may be similar to stent 350, having a plurality of struts 452 that form cells 454 connected to one another in one or more annular rows around stent 450. Stent 450 includes two annular rows of cells 454 of substantially similar size and shape, with nine cells in each row. As illustrated, cells 454 are generally diamond shaped. However, it should be understood that a different number of rows of cells 454, as well as a different number of cells 454 per row, may be suitable. As discussed in relation to stent 350, stent 450 may be formed from a shape memory alloy, such as nitinol. The struts 452 forming stent 450 may have a cross-section of between about 0.020 inches (0.51 mm) and about 0.025 inches (0.64 mm), although other dimensions may be suitable. Forming stent 450 from struts 452 of a relatively large cross-section may provide increased stiffness to stent 450, which may provide certain benefits, such as minimizing the deflection of commissure attachment features (CAFs) 466 during normal operation of prosthetic heart valve 400. On the other hand, forming stent 450 from struts 452 of a relatively small cross-section may provide increased flexibility to stent 450, which may provide certain benefits, such as the capability to be collapsed to a smaller profile during delivery.

Prosthetic heart valve 400 may also include a valve assembly 460 including three leaflets 462 attached to a cylindrical cuff 464 similar to that shown and described with reference to FIGS. 3A-B. It should be understood that although native mitral valve 130 has two leaflets 136, 138, prosthetic heart valve 400 may have three leaflets 462, or more or fewer than three leaflets, provided that the leaflets act to allow one-way antegrade blood flow through prosthetic heart valve 400, but obstruct retrograde blood flow through the prosthetic heart valve. Prosthetic heart valve 400 may have the same number of leaflets 462 as CAFs 466, each CAF providing a point of attachment of adjacent leaflets to stent 450. It should be understood that prosthetic heart valve 400 may alternatively include a pair of prosthetic leaflets and a corresponding pair of CAFs.

As with stent 350, stent 450 may be expandable to provide a radial force to assist with positioning and stabilizing prosthetic heart valve 400 in the native mitral valve annulus. However, prosthetic valve 400 includes additional securement features in the form of anchor arms 470 to help prevent an implanted prosthetic heart valve 400 from migrating into left atrium 122. Anchor arms 470 may be separately attachable to stent 450 such that, with prosthetic heart valve 400 properly positioned in the native mitral valve annulus, they hook under native mitral valve leaflets 136, 138. Alternatively, anchor arms 470 may be cut directly into stent 450, for example, via laser cutting.

Figure 4B:
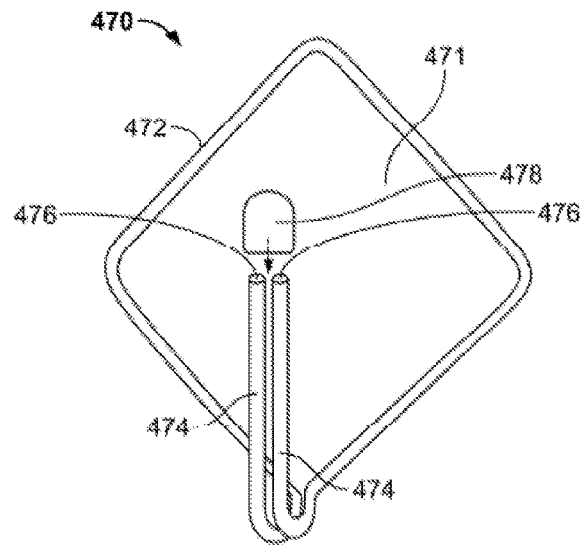
FIG. 4B is an isolated perspective view of an anchor feature of the prosthetic heart valve of FIG. 4A.

A single anchor arm 470 is shown in FIG. 4B. Anchor arm 470 may be formed of a single wire 472 bent or otherwise formed into a body portion 471 having a substantially diamond shape. Wire 472 is preferably formed of a shape-memory alloy such as nitinol. In one example, wire 472 is formed of nitinol having a diameter of about 0.015 inches (0.38 mm). As with struts 452 of stent 450, the diameter of wire 472 may be increased to provide increased stiffness or decreased to provide increased flexibility. Although the shape of body portion 471 may vary, it preferably corresponds to the geometry of a single cell 454 of stent 450. Wire 472 has two free end portions 474 that extend adjacent and substantially parallel to one another, and that are curved or hooked so as to lie at a spaced distance radially outward from body portion 471. Preferably, the tip 476 of each free end portion 474 is blunt and/or rounded to reduce the likelihood of tips 476 damaging the native tissue hooked by anchor arm 470. In addition or alternatively, a blunted and/or rounded end cap 478 may be assembled over or onto the tips 476 of free end portions 474 and fixed to tips 476, for example by welding, to provide an atraumatic tissue contact surface.

Figure 4C:
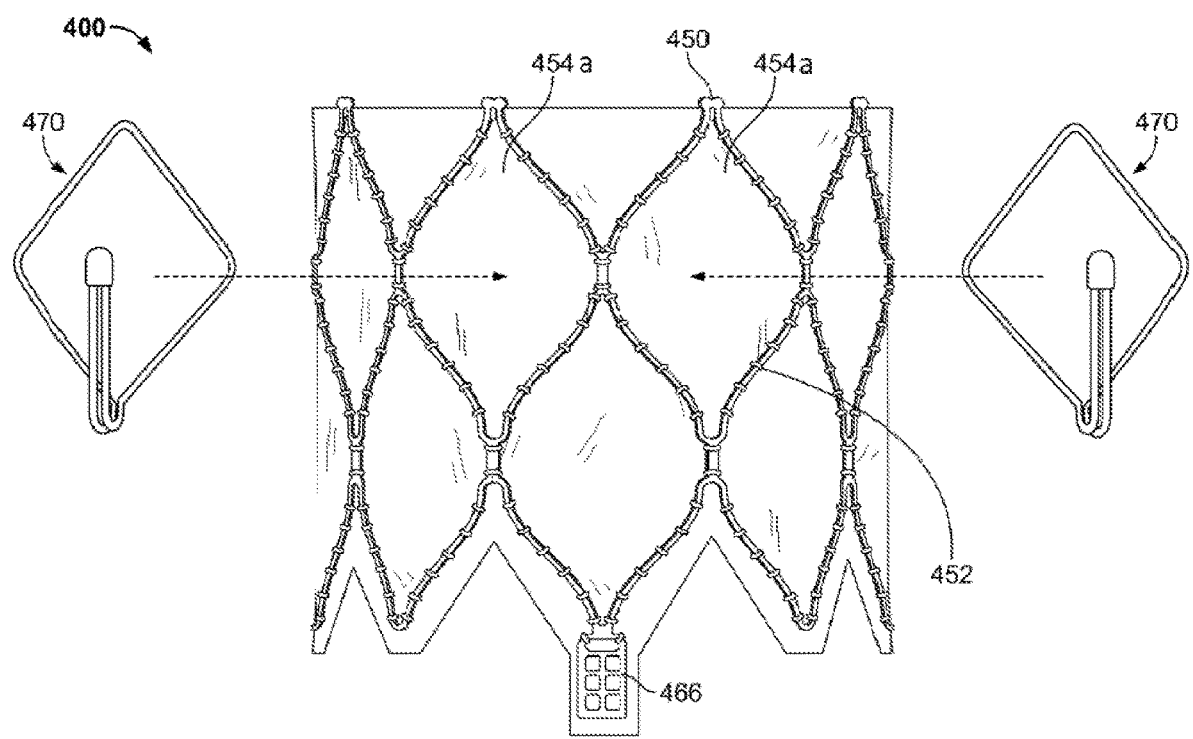
FIG. 4C is a side view of the prosthetic heart valve of FIG. 4A in a stage of manufacture.

Prosthetic heart valve 400 is shown at a possible intermediate stage of manufacture in FIG. 4C to better illustrate the attachment of anchor arms 470 to prosthetic heart valve 400. After cuff 464 and leaflets 462 have been attached to stent 450, anchor arms 470 may be coupled to prosthetic heart valve 400 at desired locations around stent 450. As shown in FIG. 4C, anchor arms 470 may be positioned within and/or adjacent to a selected cell 454a of stent 450 and connected to the prosthetic heart valve 400, for example by suturing body portion 471 of anchor arm 470 to the struts 452 defining the perimeter of selected cell 454a. The sutures coupling anchor arms 470 to prosthetic heart valve 400 may additionally pass through cuff 464. Forces applied to free end portions 474 are transmitted to the body portion 471 of anchor arm 470. With the above-described configuration of anchor arm 470 and its attachment to cell 454a, those transmitted forces are distributed over a larger area of stent 450, providing better reinforcement than if free end portions 474 were sewn or otherwise directly connected to stent 450 without the use of body portion 471.

Figure 4D:
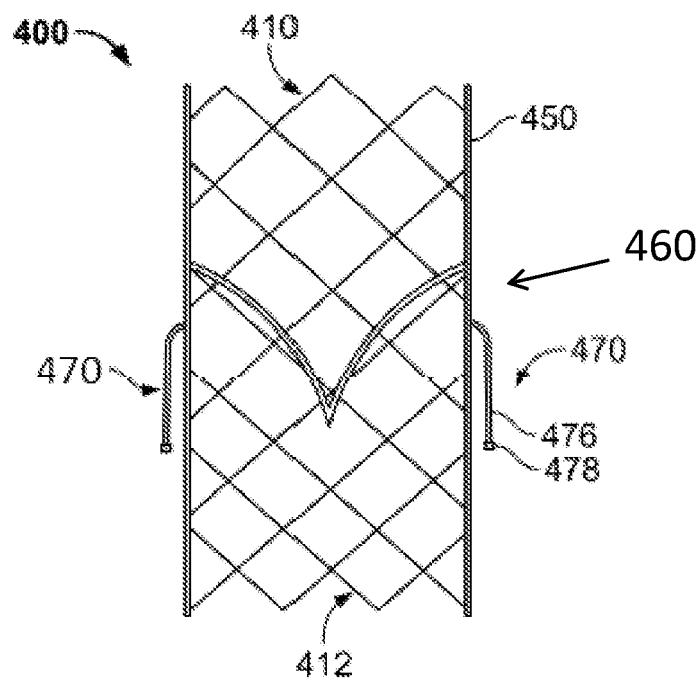
FIG. 4D is a highly schematic longitudinal cross-section of the prosthetic heart valve of FIG. 4A in a collapsed condition.
Figure 4E:
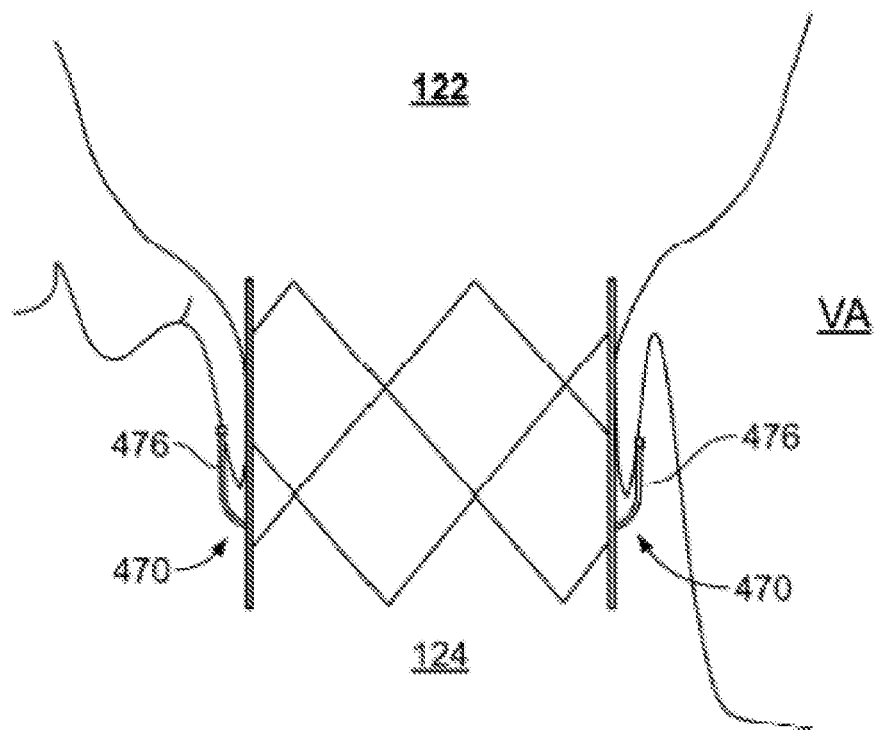
FIG. 4E is a highly schematic representation of the prosthetic heart valve of FIG. 4A implanted into a native mitral valve annulus.

As noted above, wire 472 forming anchor arms 470 is preferably made from a shape-memory alloy. By using a shape-memory alloy, the anchor arms 470 may be set, for example by heat setting, to take the illustrated shape in the absence of applied forces. However, forces may be applied to anchor arms 470 and to prosthetic heart valve 400 generally to reduce the radial size and/or bulk of the prosthetic heart valve when in the collapsed condition, which may facilitate intravascular (or other minimally invasive) delivery of the prosthetic heart valve via a delivery device (not shown). For example, as shown in FIG. 4D, prosthetic heart valve 400 may be transitioned to the collapsed condition, with free end portions 474 of anchor arms 470 being distorted or "flipped" to point toward the outflow end 412 of the prosthetic heart valve 400 rather than inflow end 410. Prosthetic heart valve 400 may be maintained in the collapsed condition, for example by a surrounding sheath of a delivery device (not shown), as prosthetic heart valve 400 is delivered to native mitral valve 130. When in a desired position relative to native mitral valve 130, prosthetic heart valve 400 may be released from the delivery device. As the constraining forces are removed from prosthetic heart valve 400, it begins to transition to the expanded condition, while anchor arms 470 move to their preset shape. Since anchor arms 470 are shape-set so that their free end portions 474 point toward inflow end 410, anchor arms 470 revert to that shape when released from the delivery device. As the free end portions 474 of anchor arms 470 transition from pointing toward outflow end 412 to pointing toward inflow end 410, native mitral valve leaflets 136, 138 are captured between the free end portions 474 and the body of stent 450, as shown in FIG. 4E. When hooked around native mitral valve leaflets 136, 138, anchor arms 470 help anchor prosthetic heart valve 400 within native valve annulus VA and are particularly effective at resisting migration of the prosthetic heart valve into left atrium 122. Distorting or flipping anchor arms 470 while prosthetic heart valve 400 is maintained in the collapsed condition may reduce the profile of the collapsed valve, although prosthetic heart valve 400 may alternatively be put in the collapsed condition without distorting or flipping anchor arms 470.

Figure 5A:
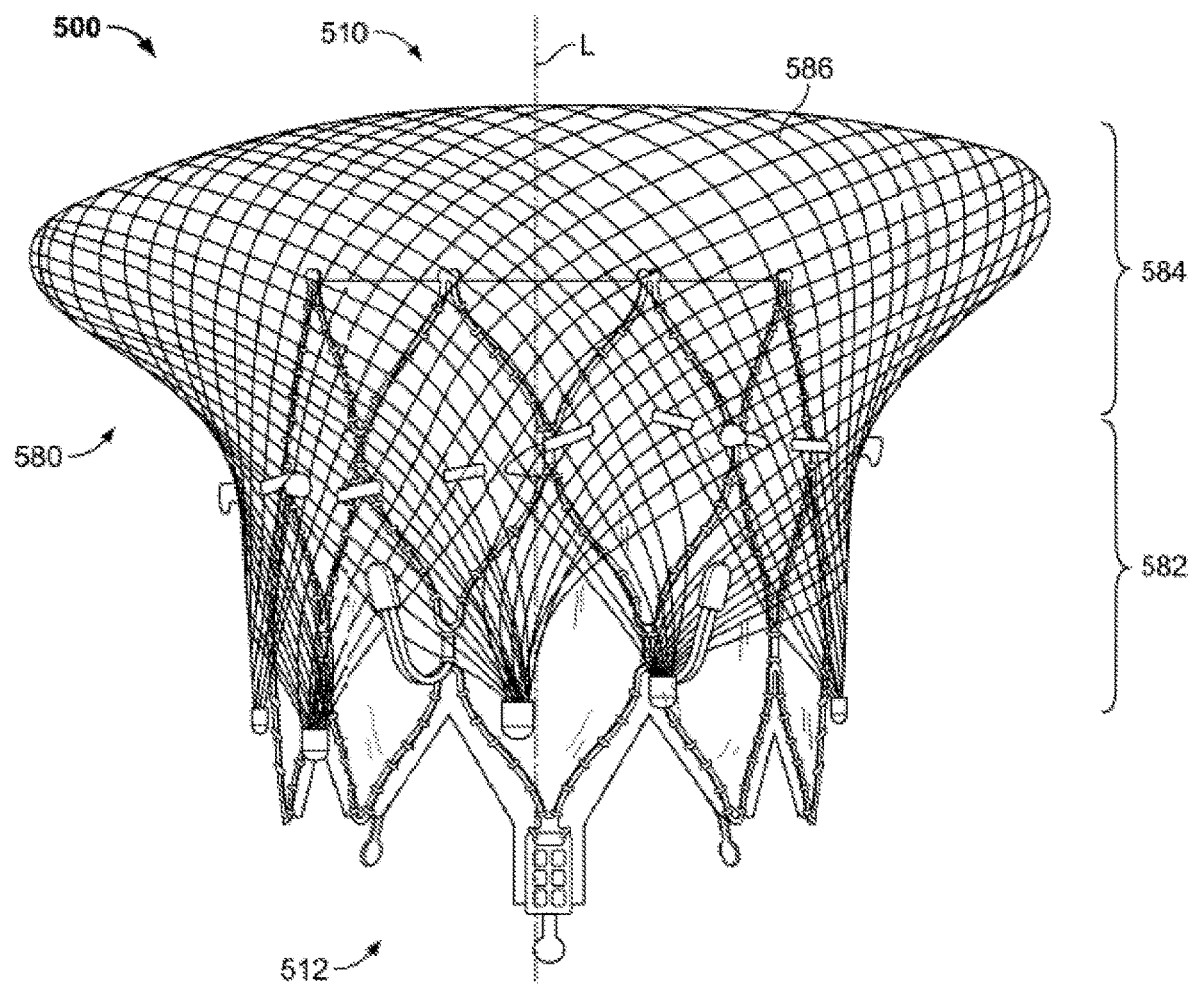
FIG. 5A is a side view of a prosthetic heart valve according to a further aspect of the disclosure.
Figure 5B:
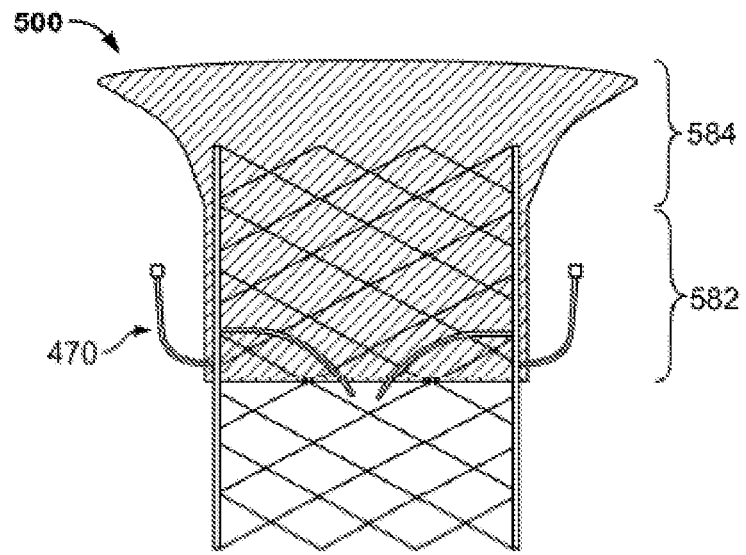
FIG. 5B is highly schematic longitudinal cross-section of the prosthetic heart valve of FIG. 5A in an expanded condition.
Figure 5C:
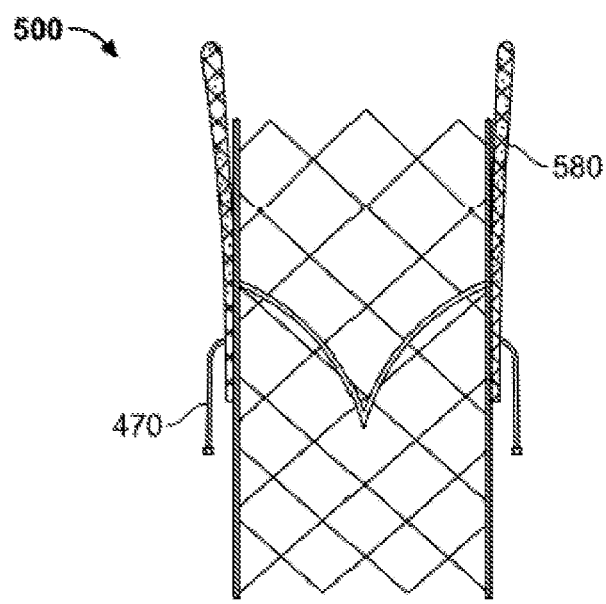
FIG. 5C is a highly schematic longitudinal cross-section of the prosthetic heart valve of FIG. 5A in a collapsed condition.

While prosthetic heart valve 400 may be used as shown and described above in connection with FIGS. 4A-E, a prosthetic heart valve may be provided with additional anchoring and/or sealing elements. For example, FIGS. 5A-C illustrate a prosthetic heart valve 500 that comprises prosthetic heart valve 400 with a flange 580 coupled thereto. Flange 580 may facilitate the anchoring of heart valve 500 within native mitral valve annulus 130 and the prevention of PV leak. Flange 580 may be formed of a material braided to create various shapes and/or geometries to engage tissue. As shown in FIGS. 5A-C, flange 580 includes a plurality of braided strands or wires 586 arranged in three dimensional shapes. In one example, wires 586 form a braided metal fabric that is resilient, collapsible and capable of heat treatment to substantially set a desired shape. One class of materials which meets these qualifications is shape-memory alloys, such as nitinol. Wires 586 may comprise various materials other than nitinol that have elastic and/or shape memory properties, such as spring stainless steel, tradenamed alloys such as Elgiloy® and Hastelloy®, CoCrNi alloys (e.g., tradename Phynox), MP35N®, CoCrMo alloys, or a mixture of metal and polymer fibers. Depending on the individual material selected, the strand diameter, number of strands, and pitch may be altered to achieve the desired shape and properties of flange 580. In the expanded condition of flange 580, the porosity of the braided fabric is such as to not interfere with the flow of blood through prosthetic heart valve 500 when the leaflets 462 thereof are in the open position.

Flange 580 may include a body portion 582 terminating at an outflow end of the flange and a flared portion 584 terminating at an inflow end of the flange. Body portion 582 may be formed with a cylindrical or tubular geometry and may be configured to be circumferentially disposed around a portion of stent 450 and/or valve assembly 460. Flange 580 may be coupled to stent 450 (and optionally to valve assembly 460 and/or cuff 464) by sutures, for example. Flange 580 alternatively or additionally may be connected to stent 450 via ultrasonic welds, glue, adhesives, or other suitable means. When coupled to stent 450, body portion 582 of flange 580 is nearer the outflow end 512 of prosthetic heart valve 500 and flared portion 584 is nearer inflow end 510. When in the expanded condition, flared portion 584 extends a greater distance radially outwardly from the longitudinal axis L of prosthetic heart valve 500 than body portion 582. In addition, the distance which flared portion 584 extends radially outwardly from longitudinal axis L may increase nearer inflow end 510.

Figure 5D:
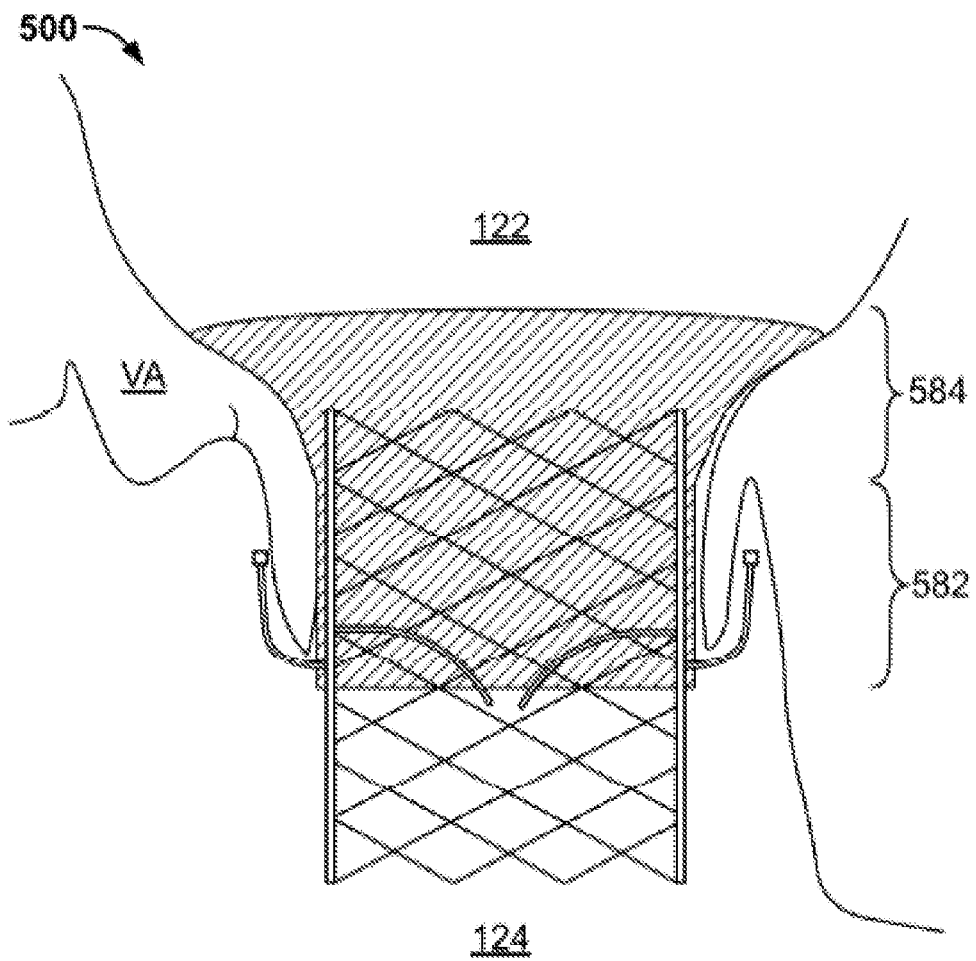
FIG. 5D is a highly schematic representation of the prosthetic heart valve of FIG. 5A implanted into a native mitral valve annulus.

Flange 580 may be preset to take the illustrated trumpet shape in the absence of external forces. As with stent 450 and anchor arms 470, flange 580 may be collapsed to a decreased profile to facilitate minimally invasive delivery. For example, prosthetic heart valve 500 may be transitioned from the expanded condition (FIGS. 5A-B) to the collapsed condition (FIG. 5C) and maintained in the collapsed condition by a surrounding sheath of a delivery device. Anchors 470 may flip and point toward the outflow end 512 of prosthetic heart valve 500 in the collapsed condition, as described in connection with FIG. 4D, and flange 580 may collapse radially inwardly and become substantially cylindrical and/or significantly less flared than in the expanded condition. Body 582 of flange 580 may be positioned between anchor arms 470 and the remainder of stent 450. Prosthetic heart valve 500 may be delivered to the implant site in the collapsed condition and, when in the desired position relative to native mitral valve 130, transitioned to the expanded condition, for example by removing the surrounding sheath of the delivery device. During the transition from the collapsed condition to the expanded condition, anchor arms 470 revert to the preset shape as described in connection with FIG. 4E, capturing native mitral valve leaflets 136, 138 between anchor arms 470 and corresponding portions of stent 450. Flange 580 also transitions from the collapsed condition to the expanded condition, assuming its preset shape shown in FIG. 5D. When implanted and in the expanded condition, flange 580 provides a large surface area to help anchor prosthetic heart valve 500 within native valve annulus VA, and may be particularly effective at resisting movement of prosthetic heart valve 500 toward left ventricle 124. Specifically, flange 580 has an expanded diameter that is too large to pass through native valve annulus VA. Because flange 580 is coupled to stent 450, prosthetic heart valve 500 is restricted from migrating into left ventricle 124 during normal operation of prosthetic heart valve 500. Thus, the combination of anchor arms 470 engaged with the mitral valve leaflets, and flange 580 engaged with the tissue on the atrial side of the mitral valve annulus, helps to securely anchor prosthetic heart valve 500 within the mitral valve annulus and limits its migration toward either the left atrium or the left ventricle.

As noted above, flange 580 may be coupled to stent 450 (and optionally to the leaflets and/or cuff) by sutures. However, there may be other desirable mechanisms to attach flange 580 to stent 450 (or otherwise to attach braided flanges similar to braided flange 580 to other stents similar to stent 450).

Figure 6A:
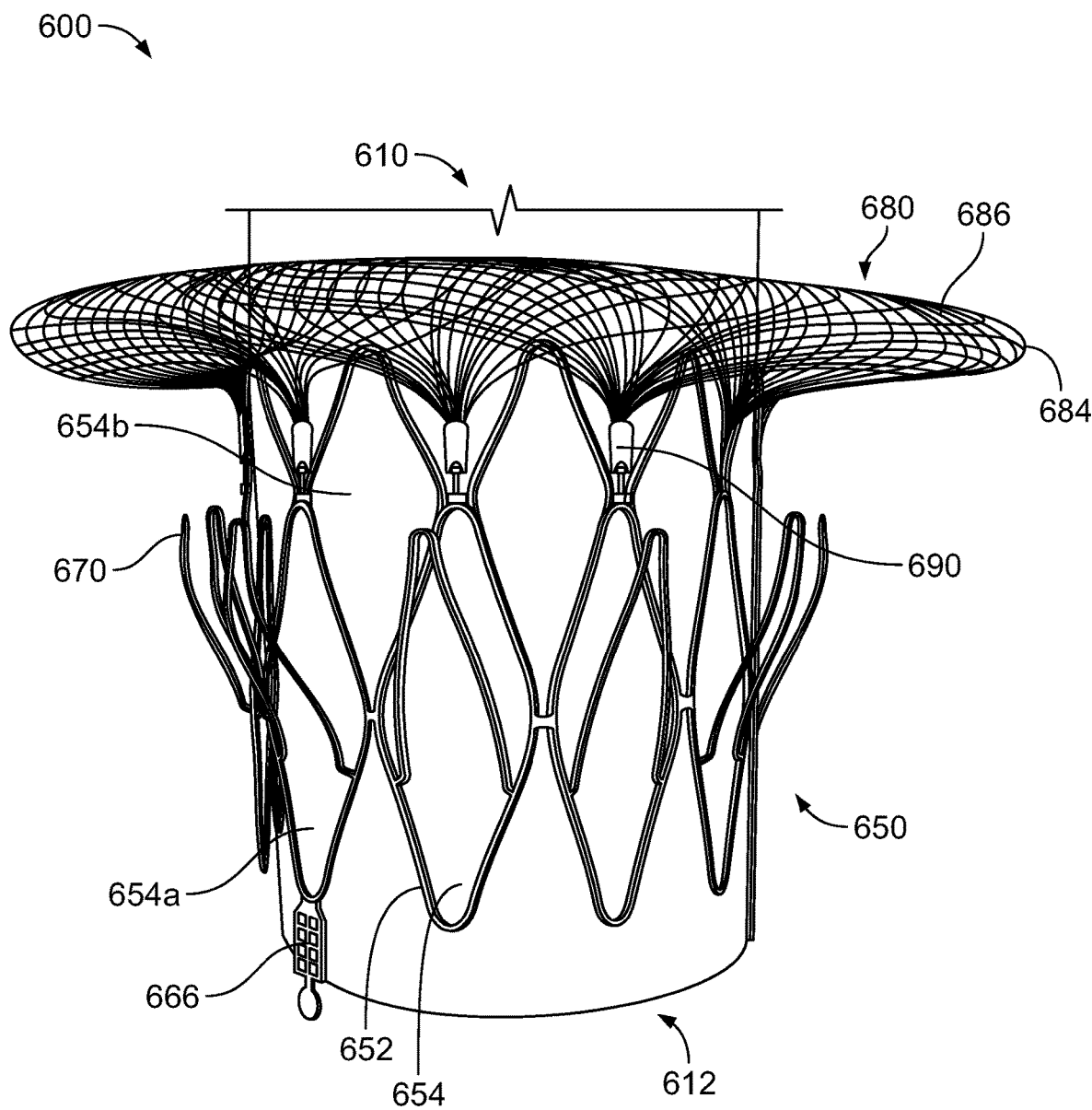
FIG. 6A is a side view of a prosthetic heart valve according to yet another aspect of the disclosure.

FIG. 6A illustrates a prosthetic heart valve 600 according to another aspect of the disclosure. Prosthetic heart valve 600 may be particularly suited for replacement of native mitral valve 130 and may be similar to prosthetic heart valve 500 in many respects. For example, prosthetic heart valve 600 may be collapsible and expandable, with a substantially cylindrical stent 650, an inflow end 610 and an outflow end 612. Stent 650 may have a plurality of struts 652 that form cells 654 connected to one another in one or more annular rows around stent 650. In the illustrated embodiment, stent 650 includes a first annular row of cells 654a adjacent outflow end 612 and a second annular row of cells 654b adjacent inflow end 610. As illustrated, cells 654 are generally diamond shaped with a substantially similar size, and each row includes nine cells. However, it should be understood that a different number of rows of cells 654, as well as a different number of cells 654 per row and a different cell shape, may be suitable. Stent 650 may be formed of any of the materials described above in connection with stents 350 and 450. In FIG. 6A, prosthetic heart valve 600 is illustrated in an expanded condition with a solid opaque tube extending through the interior of the prosthetic heart valve to more clearly illustrate the visible features of stent 650, although it should be understood that the solid opaque tube forms no part of the invention.

Prosthetic heart valve 600 may also include a valve assembly having three leaflets attached to a cylindrical cuff similar to that shown and described with reference to FIGS. 3A-B, although these elements are omitted from FIG. 6A. It should further be understood that the valve assembly of prosthetic heart valve 600 may include more or fewer than three leaflets, including the variations described above in connection with prosthetic heart valves 400 and 500. Prosthetic heart valve 600 may have the same number of leaflets as CAFs 666, each CAF providing a point of attachment for adjacent leaflets to stent 650.

Stent 650 may also include a plurality of anchor arms 670 to help prevent an implanted prosthetic heart valve 600 from migrating into left atrium 122. In the illustrated embodiment, each anchor arm 670 is formed by two struts 652, each strut having a first end extending from a cell 654 in the first row of cells 654a toward inflow end 610 where the two struts meet to form an apex at second ends of the struts. In the expanded condition of prosthetic heart valve 600, the apex of each anchor arm 670 may be positioned radially outward of the cell 654 with which the anchor arm is associated. In the collapsed condition of prosthetic heart valve 600, each anchor arm 670 may nest within the cell 654 with which the anchor arm is associated so that the anchor arm is positioned substantially within a surface defined by the associated cell. In the illustrated embodiment, each anchor arm 670 is formed integrally with stent 650, although in other embodiments, the anchor arms may be formed separately and attached to the stent. Also in the illustrated embodiment, each cell 654 in the first row of cells 654a includes an associated anchor arm 670. However, in other embodiments, fewer anchor arms 670 may be included in the first row of cells 654a, and in still other embodiments, one or more anchor arms may be provided in association with the second row of cells 654b. Anchor arms 670 may also be entirely omitted from prosthetic heart valve 600 in some embodiments, or replaced with anchor arms having a similar configuration as anchor arms 470. In use, one or more of the anchor arms 670 may clip over native mitral valve leaflets 136, 138, similar to the configuration illustrated in FIG. 5D.

Still referring to FIG. 6A, prosthetic heart valve 600 may include a braided flange 680 generally similar to flange 580 of prosthetic heart valve 500. In the illustrated embodiment, flange 680 includes a plurality of braided strands or wires 686 arranged in three dimensional shapes. Flange 680 may be formed of any of the materials described above in connection with flange 580. Although in some embodiments flange 680 may include a body portion and a flared portion similar to those in flange 580, in the illustrated embodiment flange 680 includes a flared portion 684 with no corresponding body portion or only a minimal body portion. Flared portion 684 is adapted to be positioned in left atrium 122, similar to the configuration shown in FIG. 5D. Flange 680 may be substantially similar or identical to flange 580 in most or all aspects with the exception of the omitted or minimal body portion, and the mechanism by which the flange is coupled to stent 650. Whereas flange 580 is shown as being sutured directly to the stent and/or cuff of prosthetic heart valve 500, flange 680 may be coupled to stent 650 via one or more coupling tubes 690, described in greater detail below.

Figure 6B:
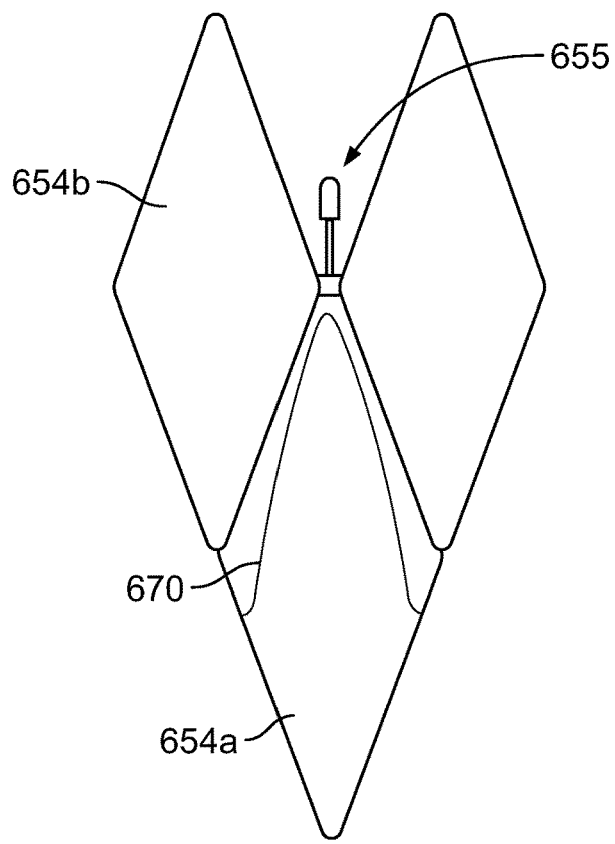
FIG. 6B is a highly schematic representation of a portion of a stent of the prosthetic heart valve of FIG. 6A.
Figure 6C:
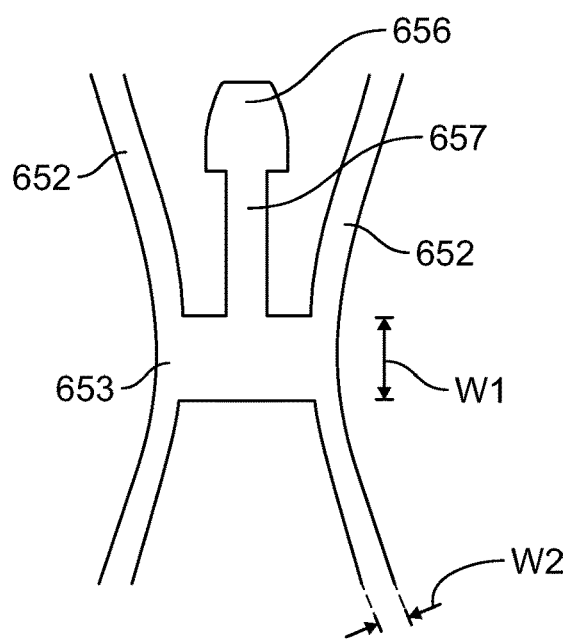
FIG. 6C is an enlarged view of a retainer of the portion of the stent shown in FIG. 6B.

FIG. 6B shows an enlarged view of two adjacent cells 654 in the second row of cells 654b, as well as a third cell in the first row of cells 654a interposed between the adjacent cells in the second row. It should be understood that the portion of stent 650 illustrated in FIG. 6B is shown prior to attachment of flange 680 to the stent. In the illustrated embodiment, stent 650 includes a plurality of receivers 655 that assist in coupling flange 680 to the stent with corresponding coupling tubes 690. FIG. 6C illustrates an enlarged view of one of the receivers 655. In the illustrated example, a connecting strut 653 connects each pair of adjacent cells 654 in the second row of cells 654b. Connecting strut 653 may have a thickness that is similar to the thickness of struts 652 forming cells 654, the thicknesses being measured between an outer or abluminal surface of stent 650 and an inner or luminal surface of the stent. The width w1 of connecting strut 653, as measured in the inflow-to-outflow direction of stent 650, may be greater than the width w2 of struts 652 forming cells 654, as measured in a direction perpendicular to a length of the struts as shown in FIG. 6C. A receiver 655 may extend from the connecting strut 653 between each pair of adjacent cells 654 in the second row of cells 654b. Receiver 655 may include a body 657 and a head 656. Body 657 has one end coupled to connecting strut 653 and extends toward inflow end 610 of stent 650 to a second end. Body 657 may have a width and thickness that are substantially similar or identical to those of struts 652. Head 656 is provided at the second end of body 657, forming corners at right angles with the body, although it should be understood that the corners may be rounded and need not be exactly 90 degrees. Head 656 is shaped generally like an isosceles trapezoid, having a relatively wide base at its connection to body 657 and a relatively narrow top facing away from body 657 and toward the inflow end 610 of the stent. However, it should be understood that head 656 need not have the exact shape of an isosceles trapezoid. Other shapes may be suitable, and the head may include rounded or soft corners rather than sharp corners. The base of head 656 may be wider than body 657 to assist in connecting coupling tube 690 to receiver 655, as described in greater detail below. It should be understood that receiver 655 is preferably integral with stent 650 and, when the stent is laser cut from a tube of material, it is preferable that the receiver is also laser cut from that same tube. However, in other embodiments, receiver 655 may be separately attached to stent 650.

Figure 6D:
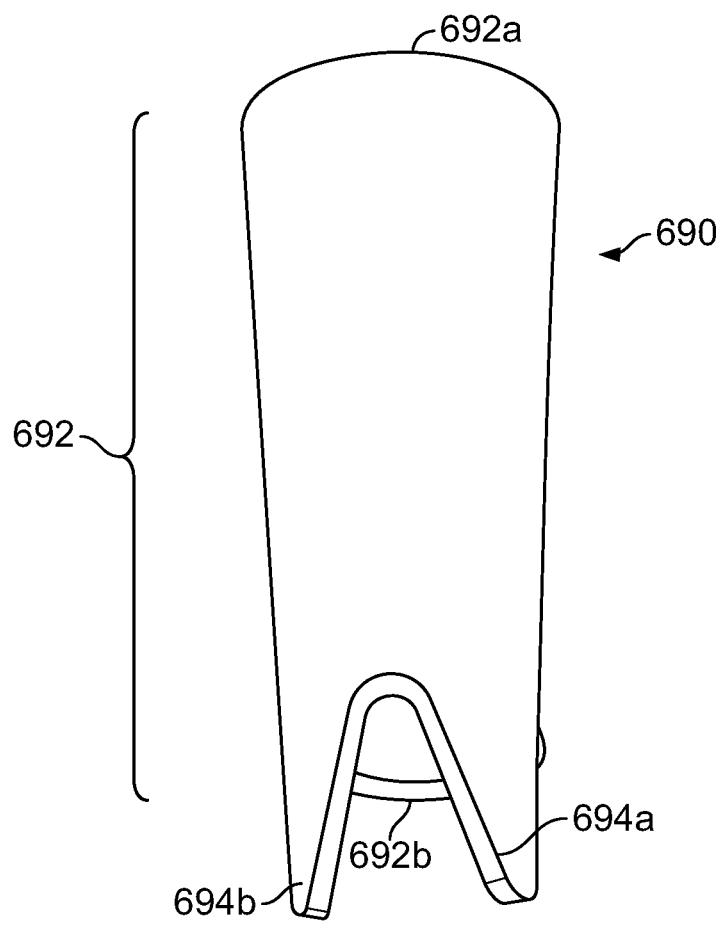
FIG. 6D is a side view of a coupling tube for attaching to the retainer shown in FIG. 6C.

FIG. 6D shows an embodiment of coupling tube 690 prior to attachment to a corresponding receiver 655 or a corresponding portion of flange 680. Coupling tube 690 may be formed from any suitable material including, for example, cobalt chromium, titanium, nitinol, or other suitable metals or alloys. In the illustrated embodiment, coupling tube 690 includes a body 692 having a tubular shape, the body extending from a first end 692a adapted to receive portions of flange 680 therein to a second opposite end 692b adapted to surround the head 656 of a corresponding receiver 655. The body 692 of coupling tube 690 may be tapered so that the inner diameter at first end 692a is larger than the inner diameter at second end 692b, although in other embodiments the body of the coupling tube may be substantially cylindrical. Coupling tube 690 also includes two prongs or feet 694a, 694b extending from the second end 692b of body 692. Each foot 694a, 694b may be substantially "U"- or "V"-shaped, with the wider end of the foot attached to the second end 692b of body 692. Feet 694a, 694b may both be positioned on the same circumferential side of the second end 692b of body 692. In other words, a transverse cross-section of body 692 at its second end 692b would have the shape of a circle, and a diameter could be drawn to split that circle into two halves such that both feet 694a, 694 extend from the same half of the circle. Preferably, the inner diameter of the second end 692b of body 692 is slightly larger than the width of the head 656 of receiver 655 at its base so that coupling tube 690 may snugly slide over the head of the receiver. Further, in the illustrated embodiment, body 692 and feet 694a, 694b are formed from an integral piece of tubing, with the feet being created by cutting the original tubing to the desired shape. This may result in the outer and inner surfaces of feet 694a, 694b having a substantially similar curvature to the outer and inner surfaces, respectively, of the second end 692b of body 692.

Figure 7A:
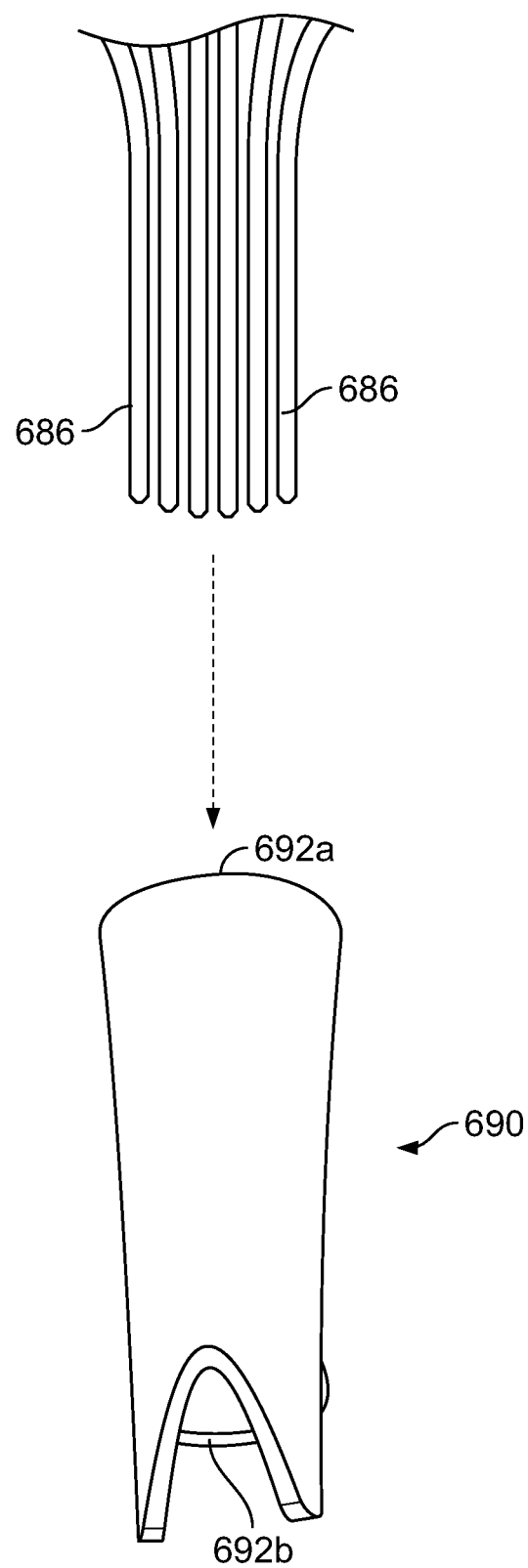
FIG. 7A illustrates a step of coupling a portion of a flange of the prosthetic heart valve of FIG. 6A to the coupling tube of FIG. 6D.
Figure 7B:
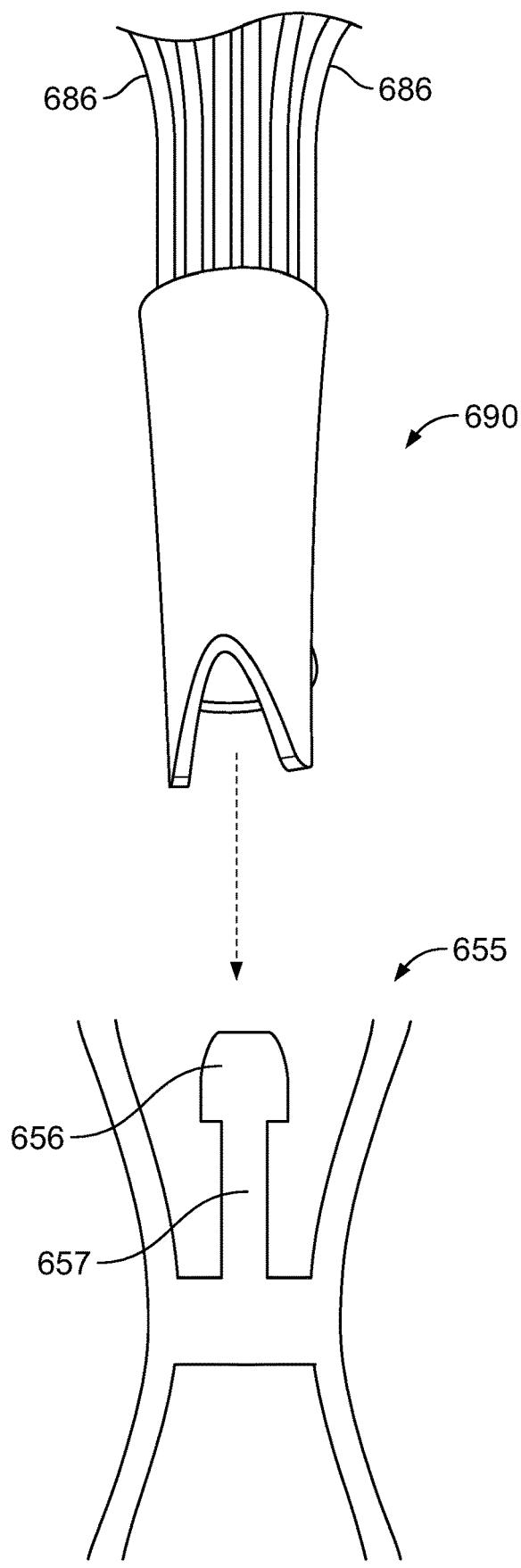
FIGS. 7B-C illustrate steps of attaching the coupling tube of FIG. 6D to the retainer of FIG. 6C.

To couple flange 680 to stent 650, individual wires 686 of flange 680, which may include free or folded ends, may be separated out from the braided arrangement of the flange. The ends of separated wires 686 may be grouped together in a plurality of bunches. Preferably, the number of bunches is equal to the total number of coupling tubes 690 used to couple flange 680 to stent 650. The ends of wires 686 may be separated from the braided arrangement of flange 680 by combing out the individual wires, which may include inserting the teeth of a comb structure into the braids of the flange and pulling the comb structure axially along a length of the flange. Although it may be desirable for the plurality of bunches to be about equally spaced around the circumference of flange 680 and for each bunch to include about the same number of individual wires 686, variations may be acceptable. A single bunch of individual wires 686 is illustrated in FIG. 7A. After wires 686 are grouped in a bunch, they may be inserted into coupling tube 690 through the first end 692a of body 692. Wires 686 may be fixed to the interior of coupling tube 690 in any suitable fashion, including, for example, by crimping the first end 692a of body 692, welding and/or via adhesives. The bunch of individual wires 686 may be coupled together prior to inserting them into coupling tube 690, for example with a band, such as a marker band, clip, or other fastener.

Figure 7C:
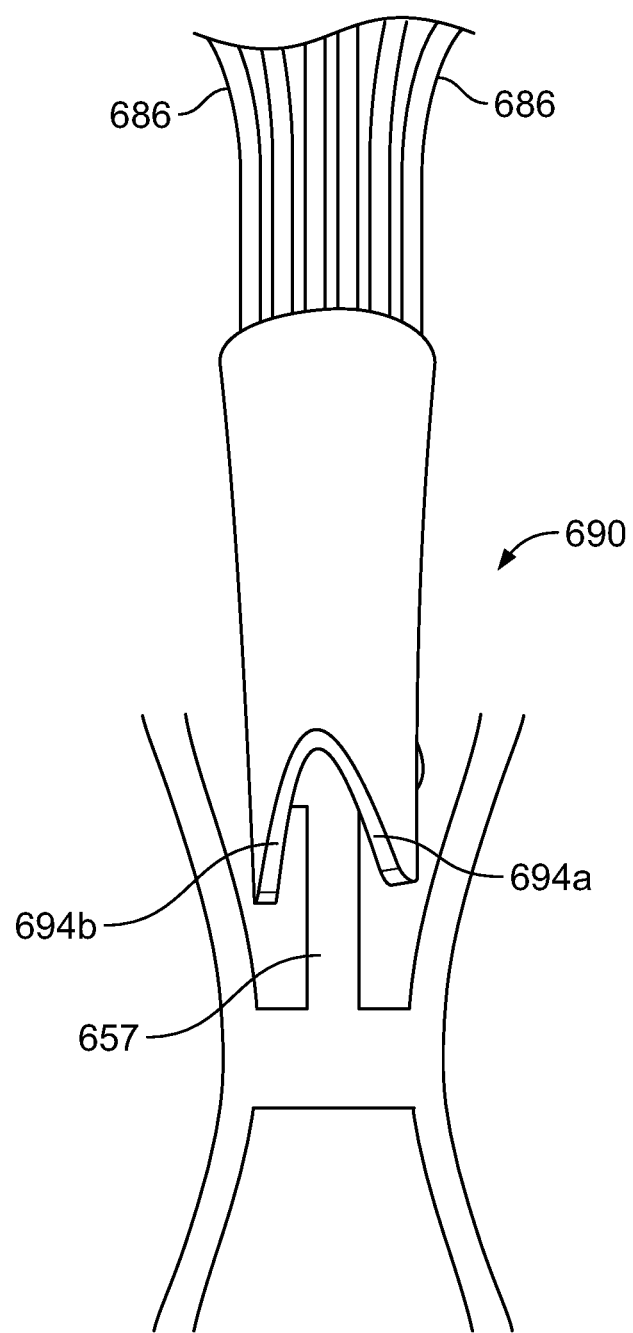
Figure 7D:
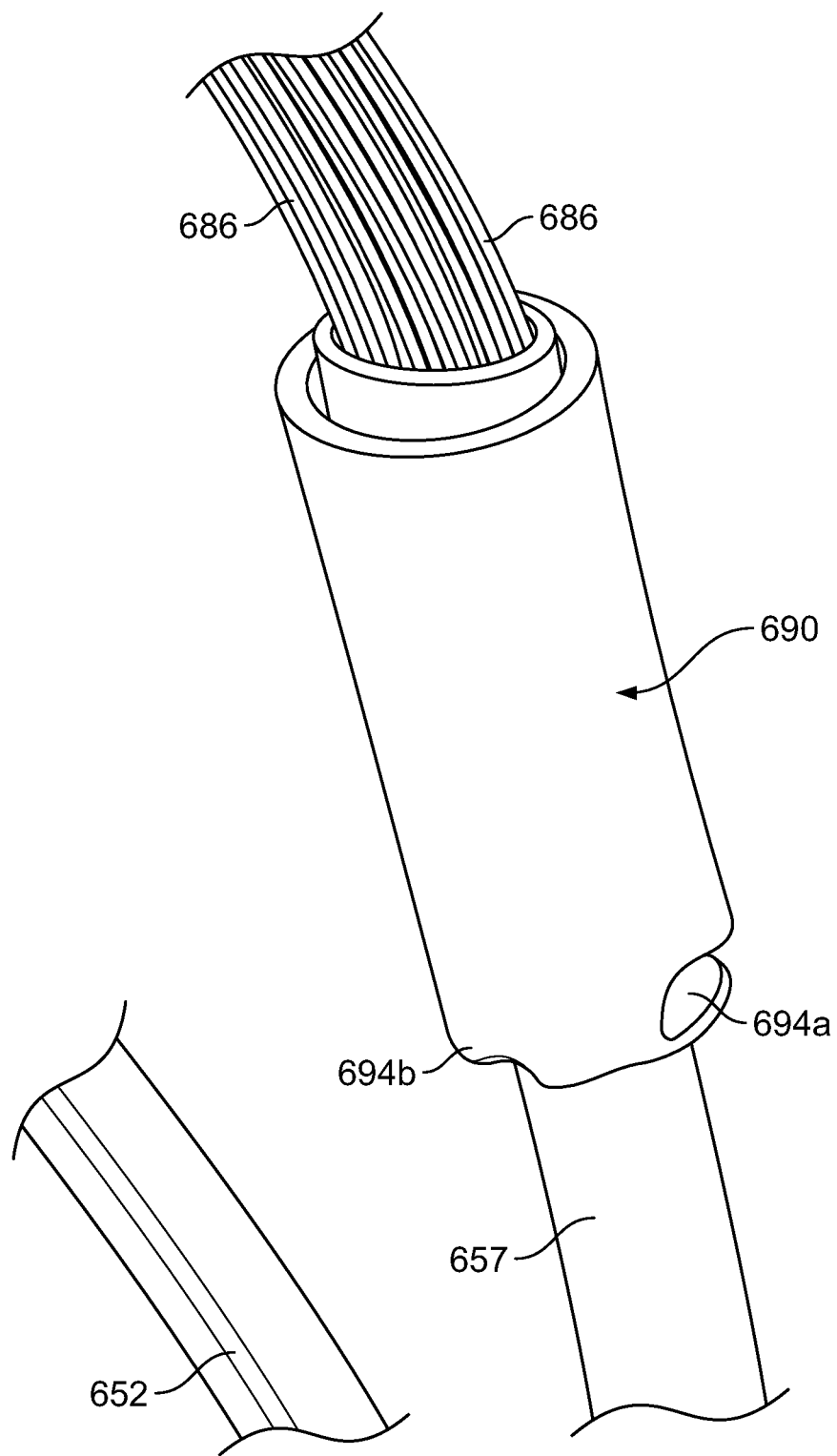
FIG. 7D is a top perspective view of the coupling tube of FIG. 6D attached to the retainer of FIG. 6C.

Once the individual wires 686 of the bunch are fixed to coupling tube 690, the second end 692b of the body 692 of the coupling tube may be slid over the head 656 of receiver 655 until the second end of the body is aligned with, or passes beyond, the transition between the head and the body 657 of the receiver, as shown in FIG. 7C. While coupling tube 690 may be slid over receiver 655 in any rotational orientation, it is particularly desirable that feet 694a, 694b are positioned radially outward of the outer surface of stent 650, for reasons described below. While coupling tube 690 is in that position, feet 694a, 694b may be bent toward the inner surface of the stent, for example about ninety degrees, with the feet on opposite sides of the body 657 of receiver 655, as shown in FIG. 7D. The configuration of feet 694a, 694b wrapping around the base of the head 656 of receiver 655 on opposite sides of body 657 helps prevent coupling tube 690 from rotating on or disconnecting from the receiver.

As noted above, it is preferable for coupling tube 690 to be coupled to receiver 655 so that feet 694a, 694b are bent toward the interior of stent 650. This is because the tips of bent feet 694a, 694b, if projecting radially outward from the stent, could damage native anatomical tissue contacting the tips of the feet, or could otherwise interfere with an overlying sheath of a delivery device, potentially damaging the sheath or preventing prosthetic heart valve 600 from being loaded into the sheath or re-sheathed. Although it is not necessary to fix the second end 692b of the body 692 of coupling tube 690 to receiver 655 beyond the bending of feet 694a, 694b, in some embodiments the coupling tube may be further fixed to the receiver by welding, adhesives, or other suitable means. However, it should be noted that avoiding such fixation may be preferable, as allowing coupling tube 690 a small amount of translation with respect to receiver 655 may help dissipate stresses that might arise for a coupling tube rigidly fixed to the receiver.

Referring back to FIG. 6A, the process of coupling one bunch of individual wires 686 of flange 680 to a receiver 655 via coupling tube 690 can be repeated for each point at which the flange is coupled to stent 650. In the illustrated example, prosthetic heart valve 600 includes nine coupling tubes 690 that couple flange 680 to stent 650 at nine locations around the periphery of the stent spaced apart by substantially equal distances in the circumferential direction. It should be understood that, although the process is described above as first coupling wires 686 to coupling tube 690, and then attaching the coupling tube to receiver 655, that order is not required. In other words, coupling tube 690 may be attached to receiver 655 first, with the corresponding bunch of wires 686 subsequently welded or otherwise fixed to the coupling tube. It should be understood that all coupling tubes 690 may be coupled to stent 650 prior to any portion of flange 680 being coupled to any of the coupling tubes, or otherwise all of the coupling tubes may be coupled to the flange prior to attaching any of the coupling tubes to the stent. Alternatively, some portions of flange 680 may be fully coupled to stent 650 via corresponding coupling tubes 690 before other portions of the flange are coupled to the stent via other coupling tubes.

Referring again to FIG. 6D, although one particular configuration for coupling tube 690 is described above, others may be acceptable. For example, the body 692 of coupling tube 690 is illustrated as tapering in inner diameter from first end 692a toward second end 692b from which feet 694a, 694b extend. This tapering may not be necessary. Preferably, the inner diameter of the second end 692b of the body 692 of coupling tube 690 is the minimum necessary to be able to pass over the head 656 of receiver 655, while the inner diameter of the first end 692a of the body of the coupling tube is the minimum necessary to receive the desired number of wires 686 and any material used to fix the wires therein. In the particular embodiment illustrated, the first end 692a of the body 692 of coupling tube 690 has a larger inner diameter to accommodate the desired number of wires 686. However, the inner diameter of the body 692 of coupling tube 690 could be tapered in the reverse direction, or otherwise have a constant inner diameter along its length, depending on (i) the size of the head 656 of receiver 655 that will be received in the second end 692b of the body of the coupling tube, and (ii) the number and size of the individual wires that will be received in the first end 692a of the body of the coupling tube. Further, although the body 692 of coupling tube 690 is illustrated with a circular transverse cross-section, such a configuration is not necessary. Although it may be generally simpler to manufacture coupling tube 690 with a circular transverse cross-section, other shapes may be desirable. For example, the second end 692b of the body 692 of coupling tube 690 may be formed to have a cross-sectional shape, such as rectangular, that substantially matches the cross-sectional shape of the head 656 of receiver 655 to provide a snug fit between the second end of the coupling tube and the head of the receiver. And while the first and second ends 692a, 692b of the body 692 of coupling tube 690 may have the same shape in transverse cross-section, such a configuration is not necessary. For example, it may be preferable for the second end 692b of the body 692 of coupling tube 690 to have a rectangular shape in transverse cross-section to match the shape of the head 656 of receiver 655, while the first end 692a of the body of the coupling tube has a circular shape in transverse cross-section for receiving and tightly holding a bunch of the individual wires 686 of flange 680.

Referring again to FIG. 6A, prosthetic heart valve 600 is illustrated with nine cells 654 in the second circumferential row 654b, with one receiver 655 positioned between each pair of adjacent cells in that row, and a coupling tube 690 attaching portions of flange 680 to each receiver. In other embodiments, there need not be a one-to-one correspondence of coupling tubes 690 to cells 654 in a given row. However, it is generally preferable that points of attachment of flange 680 to stent 650 are provided symmetrically about the circumference of the stent to substantially evenly distribute forces between the flange and the stent. Still further, although receivers 655 are illustrated as being positioned between adjacent cells 654 in the second row of cells 654b, the receivers could instead be positioned between adjacent cells in the first row of cells 654a (with connecting struts 653 positioned between adjacent cells in the first row of cells rather than the second row of cells). In other embodiments, instead of being positioned between circumferentially adjacent cells 654, receivers 655 may be positioned at apices of the cells. For example, receivers 655 may be coupled to the apex of each cell 654 in the second circumferential row of cells 654b at the inflow end 610 of stent 650. In other embodiments, receivers 655 may be coupled to the apex of each cell 654 in the first circumferential row of cells 654a adjacent the outflow end 612 of stent 650, with the receivers extending toward the inflow end 610 of the stent. The particular location of receivers 655 may depend on the desired location of flange 680 with respect to other portions of stent 650 and/or the position of the valve assembly within the stent.

Referring again to FIGS. 6B-C, receiver 655 is illustrated as having a length between the point of connection of body 657 to connecting strut 653 and the free end of head 656. Although that length is illustrated in FIG. 6B as being between about one third and about one half of the length between connecting strut 653 and the inflow end 610 of stent 650 in the expanded condition of the stent, the drawing is not intended to be to scale and receivers 655 having larger or smaller lengths may be suitable. In some embodiments, the total length of each receiver 655 may be substantially equal to one another. However, in other embodiments, receivers 655 may have different lengths. For example, by staggering the length of receivers 655, and in particular adjacent ones of the receivers, the bulk of coupling tubes 690 may be spread out to reduce the overall bulk. On the other hand, if receivers 655 all have the same length, all of the coupling tubes 690 are likely to be in line with each other when compressed into a delivery system, resulting in a potentially larger profile compared to an embodiment in which the lengths of the receivers are staggered.

Figure 8A:
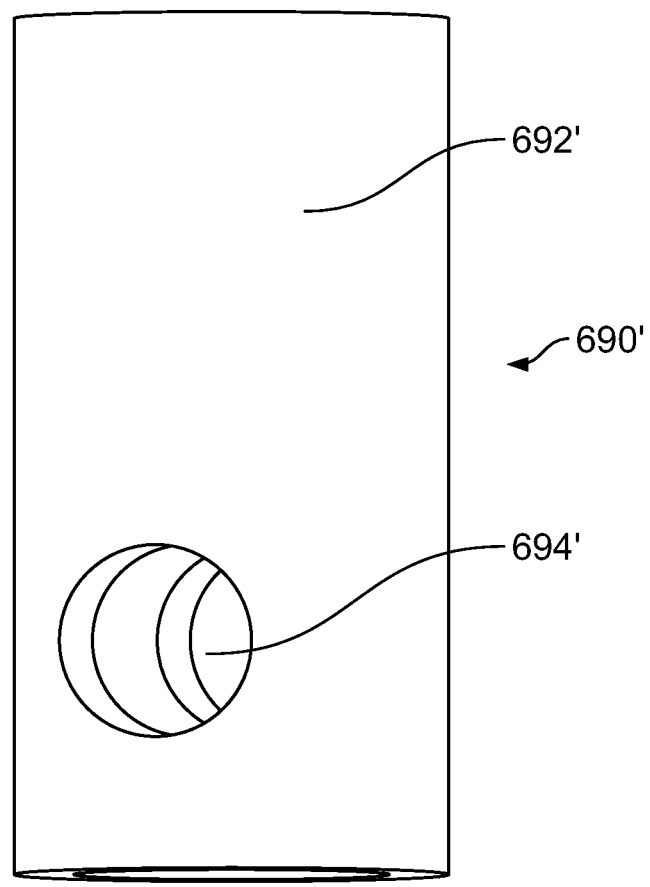
FIG. 8A is a side view of another embodiment of a coupling tube for attaching a flange of a prosthetic heart valve to a stent of the prosthetic heart valve.

Coupling tubes 690 described above rely, at least in part, on the interference between feet 694a, 694b, after they are bent, with the head 656 of receiver 655. However, other configurations may be suitable. For example, FIG. 8A illustrates an alternate version of a coupling tube 690'. Coupling tube 690' may be tubular and include a substantially cylindrical body 692' with a through-hole or aperture 694' extending transversely through the body so that a structure, such as a suture, wire, or other filament can be passed transversely through the coupling tube. Preferably, aperture 694' is positioned adjacent a longitudinal end of the body 692', as opposed to near the longitudinal center of the body.

Figure 8B:
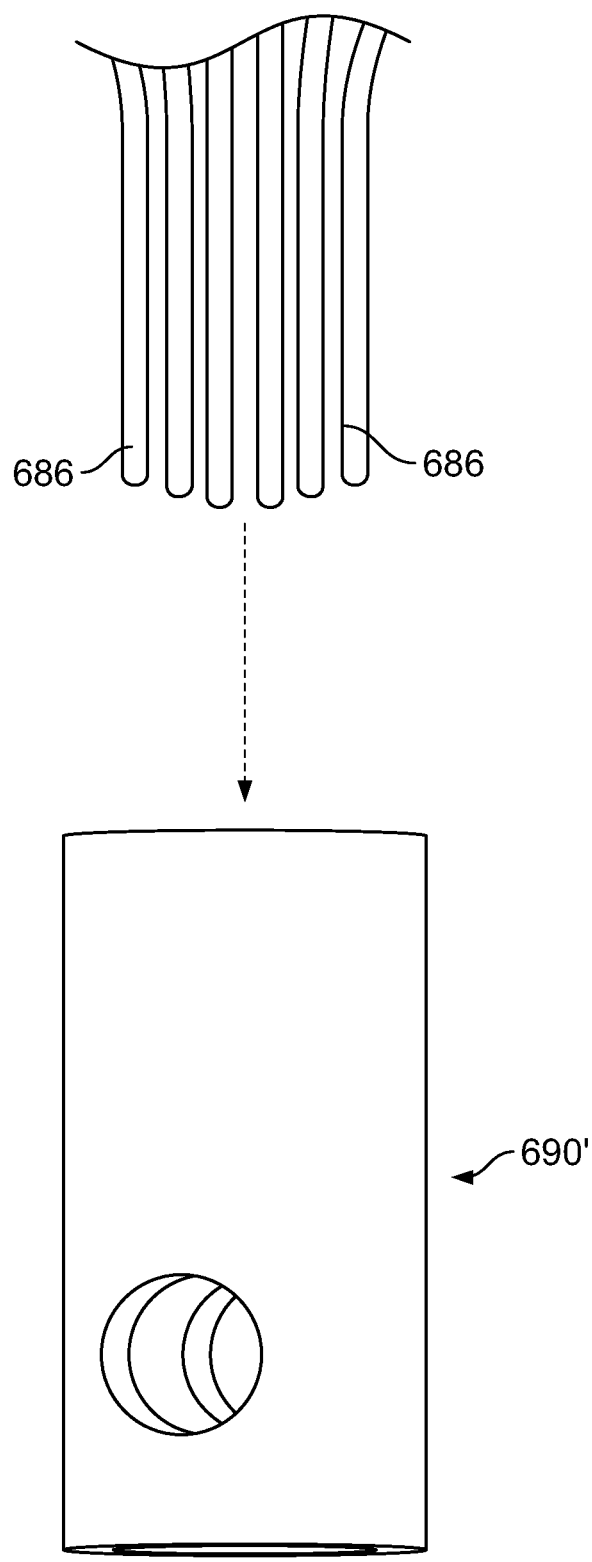
FIGS. 8B-C illustrate steps of attaching the flange of a prosthetic heart valve to the stent of the prosthetic heart valve using the coupling tube of FIG. 8A.
Figure 8C:
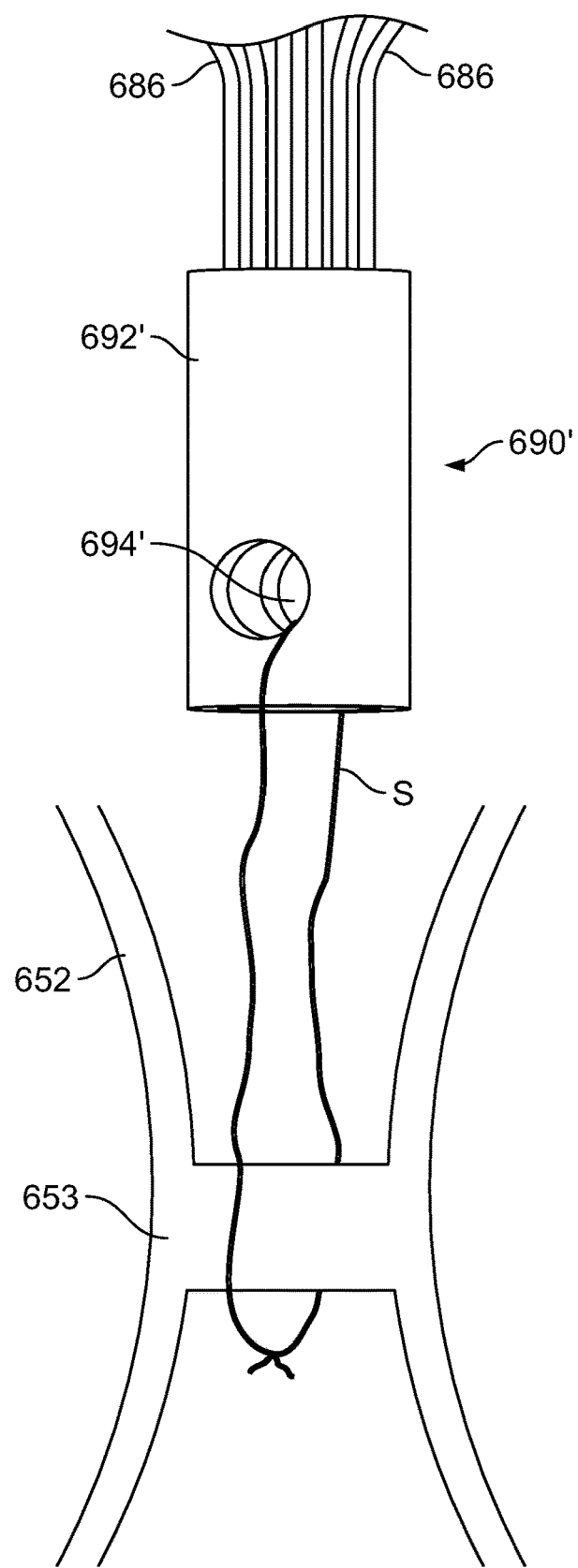

To couple flange 680 to stent 650 using coupling tubes 690', individual wires 686 of flange 680 are grouped together and fixed within the coupling tube, as shown in FIG. 8B. This may be performed in substantially the same manner as described above in connection with coupling tube 690, and is not described in further detail here. With the group of individual wires 686 fixed to the respective coupling tube 690', as shown in FIG. 8C, a connecting element such as a thread or suture S may be passed through the aperture 694' in body 692', wrapped around connecting strut 653, and tied, knotted, or otherwise secured in order to attach coupling tube 690' to connecting strut 653. It should be understood that because the embodiment of coupling tube 690' illustrated in FIGS. 8A-C does not rely on feet similar to feet 694a, 694b of coupling tube 690, the stent 650 used with coupling tubes 690' may omit retainers 655, since the main purpose of the retainers is to interact with the feet 694a, 694b of coupling tubes 690. Further, it should be understood that, as with coupling tubes 690, the attachment of flange 680 to stent 650 using coupling tubes 690' may be performed in any order. In other words, coupling tube 690' may be coupled to stent 650 with suture S prior to fixing the individual wires 686 of flange 680 to the coupling tube.

Using a suture S or other similar type of wire, thread, or filament to connect coupling tubes 690' to stent 650 may provide certain benefits. For example, a rigid connection between coupling tube 690' and stent 650 could result in portions of the stent fatiguing, for example if stresses on flange 680 are transferred to the stent via a rigidly connected coupling element. The use of a thread or suture S may significantly reduce or eliminate the transfer of stresses from flange 680 to stent 650. Further, although steps may be taken to reduce the interference of coupling tube 690 with the native anatomy and/or a delivery device used to deliver prosthetic heart valve 600, for example by folding the feet 694a, 694b of coupling tube 690 toward the interior of stent 650, coupling tube 690' and the use of a suture S to connect it to the stent may even further reduce the likelihood of any interference between coupling tube 690' and the native anatomy and/or a delivery device used to deliver the prosthetic heart valve.

As with coupling tubes 690, coupling tubes 690' may be provided in a desired number relative to the number of cells 654 of stent 650, and need not be connected to connecting struts 653 between circumferentially adjacent cells in the second row of cells 654b. Rather, coupling tubes 690' may be coupled to any portions of stent 650 that suture S or another filament may be wrapped around. These locations may include, but are not limited to, (i) portions of stent 650 at which two circumferentially adjacent cells 654 in the first row of cells 654a are attached to one another, (ii) apices at the inflow end of cells in the second circumferential row of cells 654b, and (iii) apices at the outflow end of cells in the first circumferential row of cells. The maximum distance between a coupling tube 690' and the respective portion of stent 650 to which suture S is connected may depend on the length of the suture. In some embodiments, the length of each suture S may be substantially the same so that each coupling tube 690' has a similar or the same maximum distance from the portion of stent 650 to which the coupling tube is connected. However, in other embodiments, the sutures S may have different lengths so that coupling tubes 690' have different maximum distances from the portions of stent 650 to which they are coupled.

Although coupling tubes 690 and 690' are described in connection with coupling flange 680 to stent 650, it should be understood that flange 580 could be coupled to stent 450 using the coupling tubes described herein in place of the sutures described in connection with prosthetic heart valve 500.

According to a first aspect of the disclosure, a prosthetic heart valve comprises:

a stent having a collapsed condition, an expanded condition, and a plurality of cells arranged in circumferential rows, the stent having a longitudinal axis, an inflow end and an outflow end;

a valve assembly disposed within the stent;

a flange comprising a plurality of braided wires and having a flared portion; and a plurality of coupling tubes coupling the flange to the stent so that the flared portion is adjacent the inflow end of the stent, each of the coupling tubes having a first end receiving corresponding ones of the braided wires and a second end coupled to a corresponding portion of the stent; and/or the portions of the stent to which the coupling tubes are coupled are positioned at substantially equal intervals about a circumference of the stent; and/or the stent includes a plurality of receivers, each receiver having a body coupled to the stent and a head coupled to the body, the second end of each coupling tube at least partially surrounding the head of a corresponding one of the receivers; and/or each of the receivers is formed integrally with the stent; and/or the head of each of the receivers includes a base at a transition between the body and the head, a width of the base in a circumferential direction of the stent being greater than a width of the body in the circumferential direction of the stent; and/or two feet extend from the second end of each coupling tube, the two feet being bent around the base of the head of the corresponding one of the receivers so that the body is positioned between the two feet; and/or the two feet of each of the coupling tube are bent so that a tip of each foot faces the longitudinal axis of the stent; and/or each of the coupling tubes has an inner diameter that tapers from a relatively large inner diameter at the first end of the coupling tube to a relatively small inner diameter at the second end of the coupling tube; and/or the plurality of cells are arranged in a first circumferential row of cells positioned adjacent the outflow end of the stent and a second circumferential row of cells positioned adjacent the inflow end of the stent; and/or each of the coupling tubes is directly attached to a junction between a corresponding pair of circumferentially adjacent cells in the second circumferential row of cells; and/or the body of each coupling tube is directly attached to a junction between a corresponding pair of circumferentially adjacent cells in the first circumferential row of cells; and/or each of the coupling tubes is directly attached to an apex of a corresponding cell in the second circumferential row of cells, the apex being positioned adjacent the inflow end of the stent; and/or each of the coupling tubes is directly attached to an apex of a corresponding cell in the first circumferential row of cells, the apex being positioned adjacent the outflow end of the stent; and/or each of the coupling tubes includes an aperture extending in a transverse direction through the coupling tube; and/or each of the coupling tubes is coupled to the stent by a respective filament that passes through the aperture and loops around the corresponding portion of the stent; and/or the plurality of cells are arranged in a first circumferential row of cells positioned adjacent the outflow end of the stent and a second circumferential row of cells positioned adjacent the inflow end of the stent; and/or each of the filaments loops around a junction between a corresponding pair of circumferentially adjacent cells in the second circumferential row of cells; and/or each of the filaments loops around a junction between a corresponding pair of circumferentially adjacent cells in the first circumferential row of cells; and/or each of the filaments loops around an apex of a corresponding cell in the second circumferential row of cells, the apex being positioned adjacent the inflow end of the stent; and/or each of the filaments loops around an apex of a corresponding cell in the first circumferential row of cells, the apex being positioned adjacent the outflow end of the stent.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic heart valve, comprising:
   a stent having a collapsed condition, an expanded condition, and a plurality of cells arranged in circumferential rows, the stent having a longitudinal axis, an inflow end and an outflow end;
   a valve assembly disposed within the stent;
   a flange comprising a plurality of braided wires and having a flared portion; and
   a plurality of coupling tubes coupling the flange to the stent so that the flared portion is adjacent the inflow end of the stent, each of the coupling tubes having a first end receiving corresponding ones of the braided wires and a second end coupled to a corresponding portion of the stent.

2. The prosthetic heart valve of claim 1, wherein the portions of the stent to which the coupling tubes are coupled are positioned at substantially equal intervals about a circumference of the stent.

3. The prosthetic heart valve of claim 1, wherein the stent includes a plurality of receivers, each receiver having a body coupled to the stent and a head coupled to the body, the second end of each coupling tube at least partially surrounding the head of a corresponding one of the receivers.

4. The prosthetic heart valve of claim 3, wherein each of the receivers is formed integrally with the stent.

5. The prosthetic heart valve of claim 3, wherein the head of each of the receivers includes a base at a transition between the body and the head, a width of the base in a circumferential direction of the stent being greater than a width of the body in the circumferential direction of the stent.

6. The prosthetic heart valve of claim 5, wherein two feet extend from the second end of each coupling tube, the two feet being bent around the base of the head of the corresponding one of the receivers so that the body is positioned between the two feet.

7. The prosthetic heart valve of claim 6, wherein the two feet of each of the coupling tubes are bent so that a tip of each foot faces the longitudinal axis of the stent.

8. The prosthetic heart valve of claim 6, wherein each of the coupling tubes has an inner diameter that tapers from a relatively large inner diameter at the first end of the coupling tube to a relatively small inner diameter at the second end of the coupling tube.

9. The prosthetic heart valve of claim 6, wherein the plurality of cells are arranged in a first circumferential row of cells positioned adjacent the outflow end of the stent and a second circumferential row of cells positioned adjacent the inflow end of the stent.

10. The prosthetic heart valve of claim 9, wherein each of the coupling tubes is directly attached to a junction between a corresponding pair of circumferentially adjacent cells in the second circumferential row of cells.

11. The prosthetic heart valve of claim 9, wherein each coupling tube is directly attached to a junction between a corresponding pair of circumferentially adjacent cells in the first circumferential row of cells.

12. The prosthetic heart valve of claim 9, wherein each of the coupling tubes is directly attached to an apex of a corresponding cell in the second circumferential row of cells, the apex being positioned adjacent the inflow end of the stent.

13. The prosthetic heart valve of claim 9, wherein each of the coupling tubes is directly attached to an apex of a corresponding cell in the first circumferential row of cells, the apex being positioned adjacent the outflow end of the stent.

14. The prosthetic heart valve of claim 1, wherein each of the coupling tubes includes an aperture extending in a transverse direction through the coupling tube.

15. The prosthetic heart valve of claim 14, wherein each of the coupling tubes is coupled to the stent by a respective filament that passes through the aperture and loops around the corresponding portion of the stent.

16. The prosthetic heart valve of claim 15, wherein the plurality of cells are arranged in a first circumferential row of cells positioned adjacent the outflow end of the stent and a second circumferential row of cells positioned adjacent the inflow end of the stent.

17. The prosthetic heart valve of claim 16, wherein each of the filaments loops around a junction between a corresponding pair of circumferentially adjacent cells in the second circumferential row of cells.

18. The prosthetic heart valve of claim 16, wherein each of the filaments loops around a junction between a corresponding pair of circumferentially adjacent cells in the first circumferential row of cells.

19. The prosthetic heart valve of claim 16, wherein each of the filaments loops around an apex of a corresponding cell in the second circumferential row of cells, the apex being positioned adjacent the inflow end of the stent.

20. The prosthetic heart valve of claim 16, wherein each of the filaments loops around an apex of a corresponding cell in the first circumferential row of cells, the apex being positioned adjacent the outflow end of the stent.

* * * * *